(12) United States Patent
Busch et al.

(10) Patent No.: US 8,618,154 B2
(45) Date of Patent: Dec. 31, 2013

(54) LXR MODULATORS

(75) Inventors: Brett B. Busch, San Diego, CA (US); William C. Stevens, Jr., La Jolla, CA (US); Ellen K. Kick, Pennington, NJ (US); Haiying Zhang, Pennington, NJ (US); Venkataiah Bollu, San Diego, CA (US); Richard Martin, San Diego, CA (US); Raju Mohan, Encinitas, CA (US)

(73) Assignees: Bristol-Myers Squibb Company, Princeton, NJ (US); Exelixis Patent Company LLC, South San Francisco, CA (US)

( * ) Notice: Subject to any disclaimer, the term of this patent is extended or adjusted under 35 U.S.C. 154(b) by 49 days.

(21) Appl. No.: 13/319,937

(22) PCT Filed: May 26, 2010

(86) PCT No.: PCT/US2010/036211
§ 371 (c)(1),
(2), (4) Date: Nov. 30, 2011

(87) PCT Pub. No.: WO2010/138598
PCT Pub. Date: Dec. 2, 2010

(65) Prior Publication Data
US 2012/0071534 A1    Mar. 22, 2012

Related U.S. Application Data

(60) Provisional application No. 61/181,736, filed on May 28, 2009.

(51) Int. Cl.
*A61K 31/425*    (2006.01)
*C07D 233/54*    (2006.01)

(52) U.S. Cl.
USPC ........................................ 514/400; 548/342.1

(58) Field of Classification Search
USPC ........................................ 514/400; 548/342.1
See application file for complete search history.

(56) References Cited

FOREIGN PATENT DOCUMENTS

| WO | 2007002563 A1 | 1/2007 |
| WO | WO2007002563 | * 1/2007 |
| WO | 2008073825 A1 | 6/2008 |

* cited by examiner

*Primary Examiner* — Rei-tsang Shiao
(74) *Attorney, Agent, or Firm* — Fox Rothschild LLP; Gerard P. Norton; Wansheng Jerry Liu

(57) ABSTRACT

Compounds, pharmaceutically acceptable salts, isomers, or prodrugs thereof, of the invention are disclosed, which are useful as modulators of the activity of liver X receptors (LXR). Pharmaceutical compositions containing the compounds and methods of using the compounds are also disclosed.

30 Claims, No Drawings

LXR MODULATORS

CROSS-REFERENCE TO RELATED APPLICATIONS

This application is the 35 U.S.C. §371 National Phase Application of International Application Serial No. PCT/US2010/036211, filed May 26, 2010, which claims priority to U.S. Provisional Patent Application No. 61/181,736, filed May 28, 2009. The disclosures of which are hereby incorporated in their entirety by reference.

BACKGROUND OF THE INVENTION

Field of the Invention

This invention relates to compounds that modulate the activity of liver X receptors (LXRs). The invention also provides pharmaceutical compositions comprising the compounds of the invention and methods of utilizing those compositions for modulating the activity of liver X receptor. In particular, imidazole isomers and derivatives are provided for modulating the activity of LXRs.

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression.

There are three RXR genes (see, e.g., Mangelsdorf et al. (1992) *Genes Dev.* 6:329-344), coding for RXRα, β, and γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

$LXR_\alpha$ and $LXR_\beta$ $LXR_\alpha$ is found predominantly in the liver, with lower levels found in kidney, intestine, spleen and adrenal tissue (see, e.g., Willy, et al. (1995) *Gene Dev.* 9(9):1033-1045). $LXR_\beta$ is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137-3140). $LXR_\alpha$ is activated by oxycholesterol and promotes cholesterol metabolism (Peet et al. (1998) *Cell* 93:693-704). Thus, LXRs appear to play a role in, e.g., cholesterol metabolism (see, e.g., Janowski, et al. (1996) *Nature* 383:728-731).

The nuclear receptor LXR plays a critical role in coordinate control of bile acid, cholesterol, and triglyceride metabolism to maintain lipid homeostasis. LXRs and bile acid/oxysterol-regulated genes are potential targets for developing drug therapies for lowering serum cholesterol and treating cardiovascular and liver diseases. Compounds with activity at LXR can have profound effects on lipid homeostasis, and can more effectively control disease or disorders in which LXR is implicated. This is accomplished through regulation of multiple genes involved in cholesterol homeostasis including Cyp7a1, a member of the cytochrome p450 family of enzymes and the rate limiting step in bile acid synthesis, as well as the ABC membrane transporters ABCA1, ABCG1, ABCG5, and ABCG8. ABCA1 is critical in the efflux of cholesterol and phospholipids to lipid-poor lipoproteins such as ApoA-I thus contributing to an increase in plasma HDL levels. In addition, ABCG5 and ABCG8 appear to mediate decreased intestinal absorption of cholesterol and facilitate cholesterol efflux from liver cells into the bile. Unfortunately, in addition to the anti-atherogenic effect of LXR agonists, studies in cell culture and animal model systems have demonstrated that LXR agonists increase plasma triglyceride levels and hepatic lipogenesis and promote the increased production of VLDL lipoprotein particles. Schultz et al., Genes & Development 14:2831-2838 (2000); Repa et al. Genes & Development 14:28119-2830 (2000). Strategies to minimize the undesirable lipid effects include identifying LXRIβ selective compounds that are also partial agonists. Partial agonists can display tissue-specific activation or repression of nuclear receptors, as was demonstrated for the anti-estrogen tamoxifen, which functions as an antagonist of estrogen signaling in breast tissue and an agonist in the uterus. Characterization of LXR isoform-specific null mice indicate that LXRα is the predominant mediator of LXR activity in the liver. In macrophages, however, LXRIβ alone is sufficient to mediate the effects of LXR ligands on target gene expression. Therefore compounds with limited LXRα activity should have anti-atherogenic activity while limiting unwanted hepatic effects.

SUMMARY OF THE INVENTION

Thus, we recognized that there is a need for compounds, compositions and methods of modulating the activity of the LXR nuclear receptors in ways that separate the desirable effects on cholesterol metabolism and atherogenesis from increased plasma triglyceride levels and an increase in hepatic lipogenesis. Although full agonists of LXR cause both the desirable and undesirable effects, the present invention describes compounds that have a beneficial separation between the two, and thus have an improved therapeutic index between increased reverse cholesterol transport and detrimental effects on plasma triglycerides and LDL-cholesterol.

In one aspect, the present invention comprises compounds or an individual isomer or mixture of isomers, an isotope or a pharmaceutically acceptable salt thereof, which are useful as modulators of the activity of liver X receptors (LXRs).

Compounds for use in compositions and methods for modulating the activity of nuclear receptors are provided. In particular, compounds of the invention which are useful for modulating the liver X receptors, $LXR_\alpha$ and $LXR_\beta$, and in particular, $LXR_\beta$.

In one aspect, the compounds provided herein are agonists of LXR. In another aspect, the compounds provided herein are antagonists of LXR. Agonists that exhibit low efficacy are, in certain aspects, antagonists.

Another aspect of this invention is directed to methods of treating, inhibiting, or ameliorating the symptoms of a disease or disorder that is modulated or otherwise affected by LXR activity or in which LXR activity is implicated, comprising administering to a subject in need thereof a therapeutically effective amount of a compound of the present invention or an individual isomer or mixture of isomers or a pharmaceutically acceptable salt thereof.

Another aspect of this invention is directed to methods of modulating cholesterol metabolism to a subject in need thereof, comprising administering an effective cholesterol metabolism-modulating amount of a compound of the present invention or an individual isomer or mixture of isomers or a pharmaceutically acceptable salt thereof.

Another aspect of this invention is directed to methods of preventing or treating atherosclerosis in a subject in need thereof, comprising administering an effective cholesterol level-reducing amount of a compound of the present invention or an individual isomer or mixture of isomers or a pharmaceutically acceptable salt thereof.

Another aspect of this invention is directed to methods of modulating LXR activity to a subject in need thereof, comprising contacting the nuclear receptor with a compound of the present invention or an individual isomer or mixture of isomers or a pharmaceutically acceptable salt thereof.

Another aspect of this invention is directed to methods of treating, inhibiting or ameliorating one or more symptoms of hypocholesterolemia in a subject in need thereof, comprising administering a therapeutically effective amount of a compound of the present invention or an individual isomer or mixture of isomers or a pharmaceutically acceptable salt thereof.

Another aspect of this invention is directed to methods of increasing cholesterol efflux from cells of a subject in need thereof, comprising administering an effective cholesterol efflux-increasing amount of a compound of the present invention or an individual isomer or mixture of isomers or a pharmaceutically acceptable salt thereof.

Another aspect of this invention is directed to methods of increasing the expression of ATP-Binding Cassette A1 (ABCA1) and ATP-Binding Cassette G1 (ABCG1) in the cells of a subject in need thereof, comprising administering an effective ABCA1 and ABCG1 expression-increasing amount of a compound of the present invention or an individual isomer or mixture of isomers or a pharmaceutically acceptable salt thereof.

Another aspect of this invention is directed to methods of treating, inhibiting, or ameliorating one or more symptoms of a disease or disorder which is affected by cholesterol or bile acid levels, comprising administering to a subject in need thereof a therapeutically effective amount of a compound of the present invention or an individual isomer or mixture of isomers or a pharmaceutically acceptable salt thereof.

Another aspect of this invention is directed to pharmaceutical compositions comprising a compound of the present invention or an individual isomer or mixture of isomers or a pharmaceutically acceptable salt thereof and at least one pharmaceutically acceptable carrier or excipient.

Another aspect of this invention is directed to regulation of reverse cholesterol transport and inflammatory signaling pathways that are implicated in human disease pathology including atherosclerosis and associated diseases such as myocardial infarction and ischemic stroke in a subject in need thereof, comprising administering an effective reverse cholesterol transport and inflammatory signaling pathways regulating amount of a compound of the present invention or an individual isomer or mixture of isomers or a pharmaceutically acceptable salt thereof.

Another aspect of this invention is directed to treatment of the metabolic syndrome which comprises a constellation of disorders of the body's metabolism including obesity, hypertension, insulin resistance, and diabetes including treatment of diseases resulting from compromised metabolism and immunity including atherosclerosis and diabetes as well as autoimmune disorders and diseases in a subject in need thereof, comprising administering a therapeutically effective amount of a compound of the present invention or an individual isomer or mixture of isomers or a pharmaceutically acceptable salt thereof.

Another aspect of this invention is directed to treatment of the atherosclerosis, insulin resistance, osteoarthritis, stroke, hyperglycemia, dyslipidemia, psoriasis, age and UV exposure-dependent skin wrinkling, diabetes, cancer, Alzheimer's disease, inflammation, immunological disorders, lipid disorders, obesity, macular degeneration, conditions characterized by a perturbed epidermal barrier function, conditions of disturbed differentiation or excess proliferation of the epidermis or mucous membrane, or cardiovascular disorders in a subject in need thereof, comprising administering a therapeutically effective amount of a compound of the present invention or an individual isomer or mixture of isomers or a pharmaceutically acceptable salt thereof.

DETAILED DESCRIPTION OF THE INVENTION

In one aspect, the present invention comprises a compound of formula I,

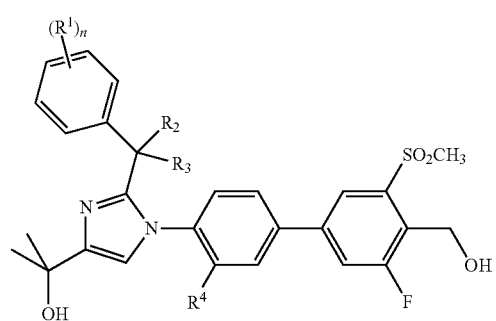

or a pharmaceutically acceptable salt thereof, wherein:
$R^1$ is chloro, fluoro, methyl or trifluoromethyl;
$R^2$ is H or methyl;
$R^3$ is H or methyl;
$R^4$ is H, chloro, fluoro, or methyl; and
n is 1, or 2.

In some embodiments, the compound of formula 1 is one in which $R^2$ and $R^3$ are methyl.

In some embodiments, the compound of formula I is one in which $R^1$ is chloro or fluoro. In some such embodiments, $R^2$ and $R^3$ are methyl.

In some embodiments, the compound of formula I is one in which $R^4$ is fluoro. In some such embodiments, $R^1$ is chloro or fluoro and $R^2$ and $R^3$ are methyl In some embodiments, the compound of formula I is one in which $R^2$ and $R^3$ are H. In some such embodiments, $R^1$ is chloro or fluoro.

In some embodiments, the compound of formula I is one in which $R^2$ is methyl and $R^3$ is H. In some such embodiments, n is 2, $R^1$ is chloro, and $R^4$ is fluoro.

In another aspect, the invention comprises a compound of structural formula I according to any of the foregoing embodiments together with one or more pharmaceutically acceptable carriers, excipients, or diluents.

In another aspect, the invention comprises a method of treating a disease or disorder comprising administering to a subject in need thereof a therapeutically effective amount of (a) a compound of structural formula I according to any of the foregoing embodiments or (b) a pharmaceutical composition comprising a compound of structural formula I according to any of the foregoing embodiments together with one or more pharmaceutically acceptable carriers, excipients, or diluents, wherein the disease or disorder is atherosclerosis, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, or cardiovascular disorders.

In some embodiments, the disease or disorder for treatment is hypercholesterolemia, hyperlipoproteinemia, hypertriglyceridemia, lipodystrophy, hyperglycemia, atherosclerosis, diabetes mellitus, or dyslipidemia.

In another embodiment, the present invention comprises a compound, isotope, or pharmaceutically acceptable salt thereof, selected from:

| No. | Name |
|---|---|
| 1 | 2-(1-(3'-fluoro-4'-(hydroxymethyl)-5'-(methylsulfonyl)biphenyl-4-yl)-2-(2-(2-fluorophenyl)propan-2-yl)-1H-imidazol-4-yl)propan-2-ol; |
| 2 | 2-(2-(2-(2-chloro-6-fluorophenyl)propan-2-yl)-1-(3'-fluoro-4'-(hydroxymethyl)-3-methyl-5'-(methylsulfonyl)biphenyl-4-yl)-1H-imidazol-4-yl)propan-2-ol; |
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol; |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 6 | 2-(2-(2-(2-Chloro-phenyl)propan-2-yl)-1-(3,3'-difluoro-4'-hydroxymethyl-5'-(methylsulfonyl)biphenyl-4-yl)-1H-imidazol-4-yl)-propan-2-ol; |
| 7 | 2-(2-(2-(2-chloro-6-fluorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 8 | 2-{1-(3,3'-Difluoro-4'-hydroxymethyl-5''-methanesulfonyl-biphenyl-4-yl)-2-[2-(2-fluorophenyl)propan-2-yl]-1H-imidazol-4-yl}-propan-2-ol; |
| 9 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 10 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}CD_3)_2$]propan-2-ol; |
| 11 | 2-(2-(2,4-dichlorobenzyl)-1-(3,3'-difluoro-4'-(hydroxymethyl)-5'-(methylsulfonyl)biphenyl-4-yl)-1H-imidazol-4-yl)propan-2-ol; |
| 12 | 2-(1-(3,3'-difluoro-4'-(hydroxymethyl)-5'-(methylsulfonyl)biphenyl-4-yl)-2-(2-(trifluoromethyl)benzyl)-1H-imidazol-4-yl)propan-2-ol; |
| 13 | 2-(1-(3-chloro-3'-fluoro-4'-(hydroxymethyl)-5'-(methylsulfonyl)biphenyl-4-yl)-2-(2-chloro-4-fluorobenzyl)-1H-imidazol-4-yl)propan-2-ol; |
| 14 | 2-(2-(2-chloro-4-fluorobenzyl)-1-(3,3'-difluoro-4'-(hydroxymethyl)-5'-(methylsulfonyl)biphenyl-4-yl)-1H-imidazol-4-yl)propan-2-ol; |
| 15 | 2-(2-(2,4-dichlorobenzyl)-1-(3'-fluoro-4'-(hydroxymethyl)-5'-(methylsulfonyl)biphenyl-4-yl)-1H-imidazol-4-yl)propan-2-ol; |
| 16 | 2-(1-(3,3'-difluoro-4'-(hydroxymethyl)-5'-(methylsulfonyl)biphenyl-4-yl)-2-(2-fluorobenzyl)-1H-imidazol-4-yl)propan-2-ol; |
| 17 | 2-(1-(3'-fluoro-4'-(hydroxymethyl)-5'-(methylsulfonyl)biphenyl-4-yl)-2-(2-methylbenzyl)-1H-imidazol-4-yl)propan-2-ol; |
| 18 | 2-(2-(2,6-dichlorobenzyl)-1-(3'-fluoro-4'-(hydroxymethyl)-5'-(methylsulfonyl)biphenyl-4-yl)-1H-imidazol-4-yl)propan-2-ol; |
| 19 | 2-[2-(2-Chloro-5-fluoro-benzyl)-1-(3'-fluoro-4'-hydroxymethyl-5'-methanesulfonyl-biphenyl-4-yl)-1H-imidazol-4-yl]-propan-2-ol; |
| 20 | 2-[2-(2-Chloro-benzyl)-1-(3,3'-difluoro-4'-hydroxymethyl-5'-methanesulfonyl-biphenyl-4-yl)-1H-imidazol-4-yl]-propan-2-ol; or |
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol. |

In another embodiment, the present invention comprises a compound, isotope, or pharmaceutically acceptable salt thereof, selected from:

| No. | Name |
|---|---|
| 1 | 2-(1-(3'-fluoro-4'-(hydroxymethyl)-5'-(methylsulfonyl)biphenyl-4-yl)-2-(2-(2-fluorophenyl)propan-2-yl)-1H-imidazol-4-yl)propan-2-ol; |
| 2 | 2-(2-(2-(2-chloro-6-fluorophenyl)propan-2-yl)-1-(3'-fluoro-4'-(hydroxymethyl)-3-methyl-5'-(methylsulfonyl)biphenyl-4-yl)-1H-imidazol-4-yl)propan-2-ol; |
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol; |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 6 | 2-(2-(2-(2-Chloro-phenyl)propan-2-yl)-1-(3,3'-difluoro-4'-hydroxymethyl-5'-(methylsulfonyl)biphenyl-4-yl)-1H-imidazol-4-yl)-propan-2-ol; |
| 7 | 2-(2-(2-(2-chloro-6-fluorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 8 | 2-{1-(3,3'-Difluoro-4'-hydroxymethyl-5'-methanesulfonyl-biphenyl-4-yl)-2-[2-(2-fluorophenyl)propan-2-yl]-1H-imidazol-4-yl}-propan-2-ol; or |
| 9 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol. |

In another embodiment, the present invention comprises a compound, isotope, or pharmaceutically acceptable salt thereof, selected from:

| No. | Name |
|---|---|
| 11 | 2-(2-(2,4-dichlorobenzyl)-1-(3,3'-difluoro-4'-(hydroxymethyl)-5'-(methylsulfonyl)biphenyl-4-yl)-1H-imidazol-4-yl)propan-2-ol; |
| 12 | 2-(1-(3,3'-difluoro-4'-(hydroxymethyl)-5'-(methylsulfonyl)biphenyl-4-yl)-2-(2-(trifluoromethyl)benzyl)-1H-imidazol-4-yl)propan-2-ol; |

-continued

| No. | Name |
|---|---|
| 13 | 2-(1-(3-chloro-3'-fluoro-4'-(hydroxymethyl)-5'-(methylsulfonyl)biphenyl-4-yl)-2-(2-chloro-4-fluorobenzyl)-1H-imidazol-4-yl)propan-2-ol; |
| 14 | 2-(2-(2-chloro-4-fluorobenzyl)-1-(3,3'-difluoro-4'-(hydroxymethyl)-5'-(methylsulfonyl)biphenyl-4-yl)-1H-imidazol-4-yl)propan-2-ol; |
| 15 | 2-(2-(2,4-dichlorobenzyl)-1-(3'-fluoro-4'-(hydroxymethyl)-5'-(methylsulfonyl)biphenyl-4-yl)-1H-imidazol-4-yl)propan-2-ol; |
| 16 | 2-(1-(3,3'-difluoro-4'-(hydroxymethyl)-5'-(methylsulfonyl)biphenyl-4-yl)-2-(2-fluorobenzyl)-1H-imidazol-4-yl)propan-2-ol; |
| 17 | 2-(1-(3'-fluoro-4'-(hydroxymethyl)-5'-(methylsulfonyl)biphenyl-4-yl)-2-(2-methylbenzyl)-1H-imidazol-4-yl)propan-2-ol; |
| 18 | 2-(2-(2,6-dichlorobenzyl)-1-(3'-fluoro-4'-(hydroxymethyl)-5'-(methylsulfonyl)biphenyl-4-yl)-1H-imidazol-4-yl)propan-2-ol; |
| 19 | 2-[2-(2-Chloro-5-fluoro-benzyl)-1-(3'-fluoro-4'-hydroxymethyl-5'-methanesulfonyl-biphenyl-4-yl)-1H-imidazol-4-yl]-propan-2-ol; or |
| 20 | 2-[2-(2-Chloro-benzyl)-1-(3,3'-difluoro-4'-hydroxymethyl-5'-methanesulfonyl-biphenyl-4-yl)-1H-imidazol-4-yl]-propan-2-ol. |

In another embodiment, the present invention comprises a compound, isotope, or pharmaceutically acceptable salt thereof, selected from:

| No. | Name |
|---|---|
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol; |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 9 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol; or |
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol. |

In another embodiment, the present invention comprises a compound, isotope, or pharmaceutically acceptable salt thereof, which is 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol.

In another embodiment, the present invention comprises a compound, isotope, or pharmaceutically acceptable salt thereof, which is 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol.

In another embodiment, the present invention comprises a compound, isotope, or pharmaceutically acceptable salt thereof, which is 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol.

In another embodiment, the present invention comprises a compound, isotope, or pharmaceutically acceptable salt thereof, which is 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol.

In another embodiment, the present invention comprises a compound, isotope, or pharmaceutically acceptable salt thereof, which is 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol.

The various compounds described herein, or their pharmaceutically acceptable salts, may contain one or more asymmetric centers and may thus give rise to isomers, such as enantiomers, diastereomers, and other stereoisomeric forms. Such forms may be defined, in terms of absolute stereochemistry, as (R)- or (S)-, or as (D)- or (L)- for amino acids. The present invention is meant to include all such possible individual stereoisomers and mixtures thereof, including their racemic and optically pure enantiomeric or diastereomeric forms. The compounds are normally prepared as racemates and can conveniently be used as such, or optically active (+) and (−), (R)- and (S)-, or (D)- and (L)-isomers or corresponding diastereomers may be prepared using chiral synthons or chiral reagents, or they may be resolved from racemic mixtures using conventional techniques, such as chiral chromatography or reverse phase HPLC. When the compounds described herein contain olefinic double bonds or other centers of geometric asymmetry, and unless specified otherwise, it is intended that the compounds include both E and Z geometric isomers.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H or D and $^3$H or T, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H or D, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

DEFINITIONS

The following terms and expressions used herein have the indicated meanings

"Nuclear receptor" refers to a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound. A nuclear receptor is a member of a superfamily of regulatory proteins that are receptors for various endogenous small molecules, e.g., steroids, retinoids, vitamin D and thyroid hormones. These proteins bind to cis-acting elements in the promoters of their target genes and modulate gene expression in response to a ligand. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is LXR.

"Liver X receptor" or "LXR" refers to a nuclear receptor implicated in cholesterol biosynthesis. As used herein, the term LXR refers to both $LXR_\alpha$ and $LXR_\beta$, two forms of the protein found in mammals. Liver X receptor-α or $LXR_\alpha$ refers to the receptor described in U.S. Pat. Nos. 5,571,696, 5,696,233 and 5,710,004, and Willy et al. (1995) Gene Dev. 9(9):1033-1045. Liver X receptor-β or $LXR_\beta$ refers to the receptor described in Peet et al. (1998) Curr. Opin. Genet. Dev. 8(5):571-575; Song et al. (1995) Ann. N.Y. Acad. Sci. 761:38-49; Alberti et al. (2000) Gene 243(1-2):93-103; and references cited therein; and in U.S. Pat. Nos. 5,571,696, 5,696,233 and 5,710,004.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development; or ii. relieving a disease or disorder, i.e., causing regression of the disorder.

"Subject" refers to a warm blooded animal such as a mammal, preferably a human, or a human child, which is afflicted with, or has the potential to be afflicted with one or more diseases and disorders described herein.

"Atherosclerosis" refers to a process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery disease or ischemic heart disease), cerebrovascular disease including ischemic stroke, multi-infarct dementia, and peripheral vessel disease, including intermittent claudication, and erectile dysfunction.

"Dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL).

"$EC_{50}$" refers to a dosage, concentration or amount of a particular test compound that elicits a dose-dependent response at 50% of maximal expression of a particular response that is induced, provoked or potentiated by the particular test compound.

"Cholesterol" refers to a steroid alcohol that is an essential component of cell membranes and myelin sheaths and, as used herein, incorporates its common usage. Cholesterol also serves as a precursor for steroid hormones and bile acids.

"Triglyceride(s)" or "TGs" refers to three fatty acid molecules esterified to a glycerol molecule and serve to store fatty acids which are used by muscle cells for energy production or are taken up and stored in adipose tissue.

"$IC_{50}$" refers to an amount, concentration or dosage of a particular test compound that achieves a 50% inhibition of a maximal response, such as modulation of nuclear receptor, including the $LXR_\alpha$ or $LXR_\beta$ activity, in an assay that measures such response.

"LXR" or "LXRs" refers to both $LXR_\alpha$ and $LXR_\beta$.

"$LXR_\alpha$" (LXR alpha) refers to all mammalian forms of such receptor including, for example, alternative splice isoforms and naturally occurring isoforms. Representative $LXR_\alpha$ species include, without limitation the rat (Genbank Accession NM_031627), mouse (Genbank Accession BC012646), and human (GenBank Accession No. U22662) forms of the receptor.

"$LXR_\beta$" (LXR beta) refers to all mammalian forms of such receptor including, for example, alternative splice isoforms and naturally occurring isoforms. Representative $LXR_\beta$ species include, without limitation the rat (GenBank Accession NM_031626), mouse (Genbank Accession NM_009473), and human (GenBank Accession No. U07132) forms of the receptor.

"Obese" and "obesity" refer to a Body Mass Index (BMI) greater than 27.8 kg/m² for men and 27.3 kg/m² for women (BMI equals weight (kg)/(height)² (m²).

Utility

The compounds of the invention exhibit valuable pharmacological properties and are particularly useful as LXR agonists, antagonists, inverse agonists, partial agonists and antagonists, or are selective to $LXR_\alpha$ or to $LXR_\beta$. The compounds of the invention are useful for the treatment of diseases or disorders described herein, such as those associated with, or having symptoms arising from the complications of, altered cholesterol transport, reverse cholesterol transport, fatty acid metabolism, cholesterol absorption, cholesterol reabsorption, cholesterol secretion, cholesterol excretion, or cholesterol metabolism.

These diseases include, for example, atherosclerosis, atherosclerotic cardiovascular diseases, (see, e.g., International Patent Application Publication Nos. WO 00/57915 and WO 00/37077), dyslipidemia, hyperglycemia, insulin resistance, diabetes, obesity, syndrome X (US Patent Application Publication No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retinitis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J. Lipid Res*. (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a subject with atherosclerosis or atherosclerotic cardiovascular disease manifest by clinical signs of such disease, wherein the methods comprise administering to the subject a therapeutically effective amount of a compound or composition of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a subject at risk for such an event.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a subject in need of such treatment. Additionally, the instant invention also provides a method for preventing or reducing the risk of developing hyperglycemia, insulin resistance, diabetes or syndrome X in a subject, comprising the administration of a prophylactically effective amount of a compound or composition of the present invention to a subject at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). Uncontrolled hyperglycemia is associated with increased and premature mortality due to an increased risk for macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM). Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese subjects and lipid oxidation is increased.

Premature development of atherosclerosis and an increased rate of cardiovascular and peripheral vascular diseases are characteristic features of subjects with diabetes. Hyperlipidemia is an important precipitating factor for these diseases. Hyperlipidemia is a disorder generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., Diabetes (1974), Vol. 23, pp. 105-11 (1974); and Laakso, M. and Lehto, S., Diabetes Reviews (1997), Vol. 5, No. 4, pp. 294-315). Several lipoprotein abnormalities have been described among diabetic subjects (Howard B., et al., Arteriosclerosis (1978), Vol. 30, pp. 153-162).

Further provided by this invention are methods of using the compounds of the invention to treat obesity, as well as the complications of obesity. Obesity is linked to a variety of medical disorders including diabetes and hyperlipidemia. Obesity is also a known risk factor for the development of type 2 diabetes (See, e.g., Barrett-Conner, E., Epidemol. Rev. (1989), Vol. 11, pp. 172-181; and Knowler, et al., Am. J Clin. Nutr. (1991), Vol. 53, pp. 1543-1551).

Administration and Formulation

A compound of the invention can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

A compound of the invention can be administered in any acceptable solid, semi-solid, liquid or gaseous dosage form. Acceptable dosage forms include, but are not limited to, aerosols, capsules, creams, emulsions, gases, gels, grains, liniments, lotions, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories.

A dosage form of the invention may be comprised solely of a compound of the invention or the compound of the invention may be formulated along with conventional excipients, pharmaceutical carriers, adjuvants, and/or other medicinal or pharmaceutical agents. Acceptable excipients include, but are not limited to, (a) antiadherents, such as croscarmellose sodium, crosprovidone, sodium starch glycolate, microcrystalline cellulose, starch and talc; (b) binders, such as cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac, zein and enteric agents; (d) disintegrants, such as cellulose, crosslinked polyvinyl pyrrolidone, sodium carboxymethyl cellulose, methylcellulose, microcrystalline cellulose, sodium starch glycolate and starch; (e) filling agents, such as calcium carbonate, cellulose, dibasic calcium phosphate, glucose, lactose, mannitol, sorbitol and sucrose; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Capsules may contain any of the afore listed excipients, and may additionally contain a semi-solid or liquid carrier, such as a polyethylene glycol or vegetable-based oils. Pharmaceutical carriers include soluble polymers, microparticles made of insoluble or biodegradable natural and synthetic polymers, microcapsules or microspheres, lipoproteins, liposomes and micelles.

The pharmaceutical composition may be in the form of a liquid, e.g., an elixir, syrup, solution, emulsion, suspension, or other like forms or may be presented as a dry product for reconstitution with water or other suitable vehicle before use. Liquid preparations may contain conventional additives such as (a) liquid diluents, such as water, saline, Ringer's solution, fixed oils such as synthetic mono or diglycerides, or polyethylene glycols, glycerin, propylene glycol or other solvents; (b) surfactants, suspending agents, or emulsifying agents, such as polyoxyethylene sorbitan fatty acid esters, saturated polyglycolized glycerides, monoglycerides, fatty acid esters, block copolymers of ethylene oxide and propylene oxide, polyoxyl stearates, ethoxylated castor oils, and ethoxylated hydroxystearic acids; (c) buffers, such as acetates, citrates or phosphates; (d) chelating agents, such as ethylenediaminetetraacetic acid; (e) antibacterial agents, such as benzyl alcohol or methyl paraben; (f) antioxidants, such as ascorbic acid or sodium bisulfite; (g) isotonic agents, sodium chloride or dextrose; as well as sweetening and flavoring agents, dyes and preservatives.

A pharmaceutical composition of the invention will contain a therapeutically effective amount of a compound of the invention, as an individual stereoisomer or mixture of stereoisomers, or a pharmaceutically acceptable salt thereof, with the remainder of the pharmaceutical composition comprised of one or more pharmaceutically acceptable excipients. Generally, for oral administration, a compound of the invention, as an individual stereoisomer or mixture of stereoisomers, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, as an individual stereoisomer or mixture of stereoisomers, or a pharmaceutically acceptable salt thereof will comprise from 5% to 75% by weight of a pharmaceutically acceptable composition, with the remainder of the composition comprised of one or more pharmaceutically acceptable excipients. For parenteral administration, a compound of the invention, as an individual stereoisomer or mixture of stereoisomers, or a pharmaceutically acceptable salt thereof will comprise from 0.01% to 1% by weight of a pharmaceutically acceptable composition. Methods for preparing the dosage forms of the invention are known, or will be apparent, to those skilled in this art; for example, see Remington's Pharmaceutical Sciences, 18th Ed., (Mack Publishing Company, Easton, Pa., 1990).

A therapeutically effective amount of a compound of the invention will vary depending upon a sundry of factors including the activity, metabolic stability, rate of excretion and duration of action of the compound, the age, weight, general health, sex, diet and species of the subject, the mode and time of administration of the compound, the presence of adjuvants or additional therapeutically active ingredients in a composition, and the severity of the disease for which the therapeutic effect is sought.

The compounds of the invention can be administered to human subjects at dosage levels in the range of about 0.1 to about 10,000 mg per day. A normal human adult having a body weight of about 70 kilograms can be administered a dosage in the range of from about 0.15 μg to about 150 mg per kilogram of body weight per day. Typically, a normal adult human will be administered from about 0.1 mg to about 25 mg, or 0.5 mg to about 10 mg per kilogram of body weight per day. The compounds of the invention may be administered in one or more unit dose forms. The unit doses may be administered one to four times a day, or two times a day, or once a day. In an alternate method of describing an effective dose, an oral unit dose is one that is necessary to achieve a blood serum level of about 0.05 to 20 μg/ml or about 1 to 20 μg/ml in a subject. The optimum dose of a compound of the invention for a particular subject can be determined by one of ordinary skill in the art.

Compounds of the invention, or an individual isomer or mixture of isomers or a pharmaceutically acceptable salt thereof, may also be administered simultaneously with, prior to, or after administration of one or more of the therapeutic agents described below. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the subject together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In one embodiment, the compounds of the invention are used in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, the compounds of the invention are used in combination with one or more of the following therapeutic agents in treating cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulae of these and additional HMG-CoA reductase inhibitors that can be used in combination with the compounds of the invention are described at page 87 of M. Yalpani, "Cholesterol Lowering Drugs," *Chemistry & Industry*, pp. 85-89 (5 Feb. 1996). In presently preferred embodiments, the HMG-CoA reductase inhibitor is selected from lovastatin and simvastatin.

In an additional embodiment, the compounds of the invention are used in combination with one or more of the following therapeutic agents in treating with one or more additional active diabetes agents depending on the desired target therapy (see, e.g., Turner, N. et al., Prog. Drug Res. (1998), Vol. 51, pp. 33-94; Haffner, S., Diabetes Care (1998), Vol. 21, pp. 160-178; and DeFronzo, R. et al. (eds.), Diabetes Reviews (1997), Vol. 5, No. 4). A number of studies have investigated the benefits of combination therapies with oral agents (see, e.g., Mahler, R., J. Clin. Endocrinol. Metab. (1999), Vol. 84, pp. 1165-71; United Kingdom Prospective Diabetes Study Group: UKPDS 28, Diabetes Care (1998), Vol. 21, pp. 87-92; Bardin, C. W. (ed.), Current Therapy In Endocrinology And Metabolism, 6th Edition (Mosby—Year Book, Inc., St. Louis, Mo. 1997); Chiasson, J. et al., Ann. Intern. Med. (1994), Vol. 121, pp. 928-935; Coniff, R. et al., Clin. Ther. (1997), Vol. 19, pp. 16-26; Coniff, R. et al., Am. J. Med. (1995), Vol. 98, pp. 443-451; Iwamoto, Y. et al., Diabet. Med. (1996), Vol. 13, pp. 365-370; Kwiterovich, P., Am. J. Cardiol (1998), Vol. 82 (12A), pp. 3U-17U). These studies indicate that diabetes and hyperlipidemia modulation can be further improved by the addition of a second agent to the therapeutic regimen.

In a further embodiment, the compounds of the invention are used in combination with one or more of the following therapeutic agents in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the therapeutic agents discussed above for treating atherosclerosis.

In yet another embodiment, the compounds of the invention are used in combination with one or more of the following therapeutic agents in treating obesity or obesity-related disorders. Such agents, include, but are not limited to, phenylpropanolamine, phentermine, diethylpropion, mazindol, fenfluramine, dexfenfluramine, phentiramine, β₃ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H₃ receptors, dopamine D₂ receptor modulators, melanocyte stimulating hormone, corticotrophin releasing factor, galanin and gamma amino butyric acid (GABA).

Synthesis

The compounds of the present invention may be prepared in a number of methods well known to those skilled in the art, including, but not limited to those described below, or through modifications of these methods by applying standard techniques known to those skilled in the art of organic synthesis. The compounds were named using ChemDraw Ultra 9.0 or 10.0 (CambridgeSoft). The reagents and starting materials are commercially available, or readily synthesized by well-known techniques by one of ordinary skill in the arts. It is understood that in the following description, combinations of substituents and/or variables of the depicted formulae are permissible only if such contributions result in stable compounds. Unless otherwise indicated, all compounds associated with NMR and/or mass spectra data were prepared and the NMR and mass spectra measured.

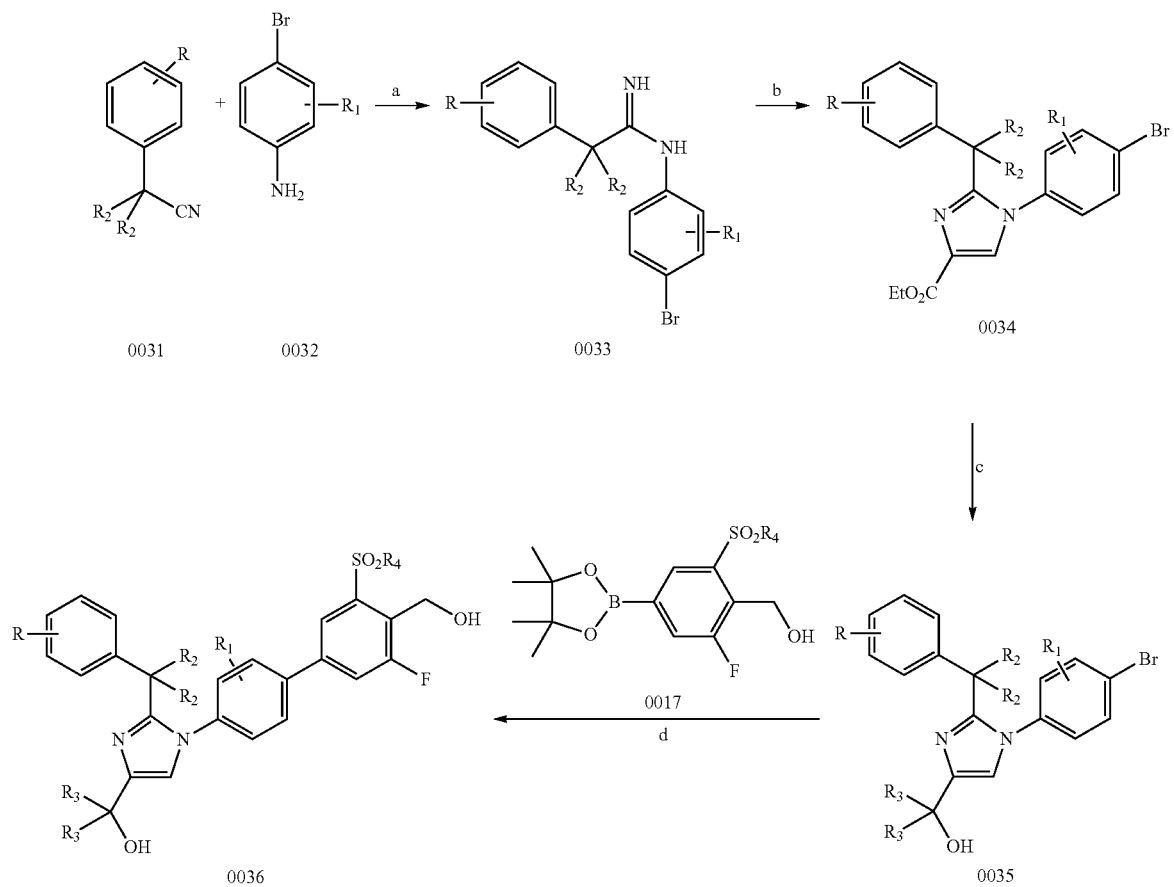

Scheme 1

(a) Me₃Al, Toluene, 0° C.-80° C.; (b) i. Ethyl bromopyruvate, NaHCO₃, THF, 70-80° C.; ii. AcOH, toluene or TFA, EtOH, 80° C.; (c) R₃MgBr, THF or THF/CH₂Cl₂,, 0° C.-rt; (d) K₂CO₃, PdCl₂(dppf), DME/H₂O, 80° C.

In general, compounds of formula (0036) are prepared by first reacting aniline of formula (0032) with 2-(phenyl)-2-methylpropanenitrile (0031) in the presence of trimethylaluminum to give compounds of formula (0033) after standard isolation procedures (Scheme 1). In a subsequent step, exposure of amidine (0033) to a haloester, such as ethyl α-bromopyruvate, under basic conditions at elevated temperature followed by dehydration conditions such as trifluoroacetic acid in ethanol provides 1H-imidazole of formula (0034) after standard isolation procedures. Compounds of formula (0034) are then subjected to functionality transformation, such as from ester to carbinol. In a palladium mediated coupling reaction, for example, Suzuki reactions, compounds of formula (0035) are then reacted with (2-fluoro-6-(sulfonyl)-4-(4,4,5,5-tetramethyl-1,3,2-dioxaborolan-2-yl)phenyl)

methanol (0017) (see Scheme 2 below) to afford compounds of formula (0036) after standard isolation procedures.

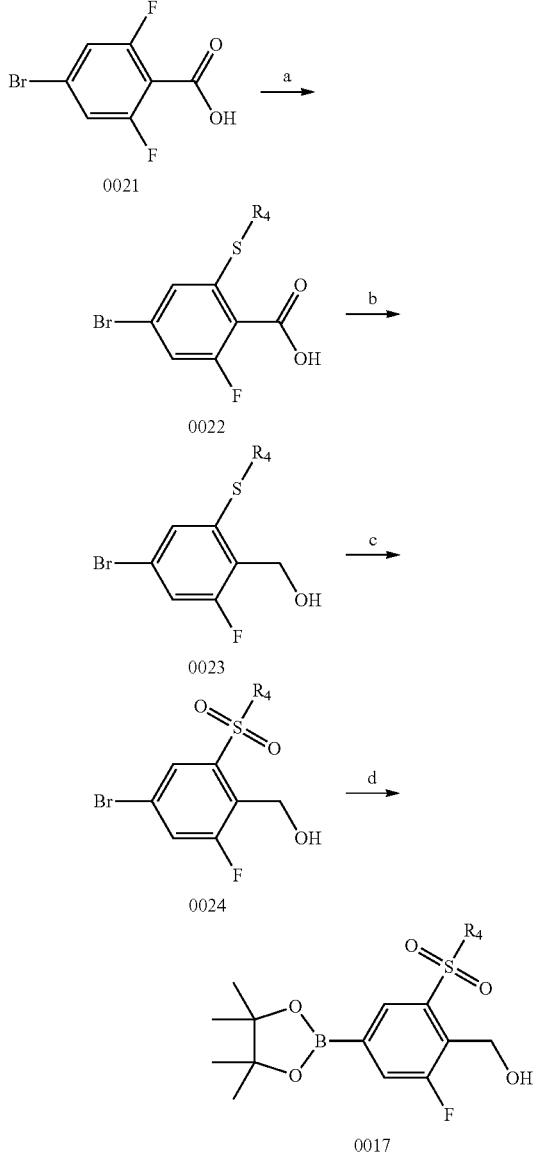

a) i. 1.0 M LHMDS in THF; ii. R$_4$SNa, reflux; b) BH$_3$-THF, 0° C.-reflux;
c) mCPBA, CH$_2$Cl$_2$; d) PdCl$_2$(dppf), bis(pinacolato)diboron, KOAc, DMSO, 80° C.

Scheme 2

Step 2a

Preparation of
4-bromo-2-fluoro-6-(methylthio)benzoic Acid

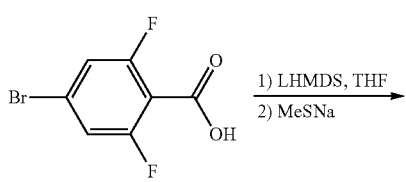

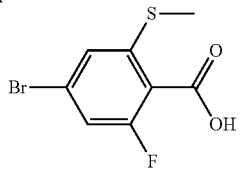

To a 500 mL round bottom flask attached with condenser was added 4-bromo-2,6-difluorobenzoic acid (16.0 g, 67.5 mmol) and anhydrous THF (110 mL). The reaction flask was cooled in an ice bath prior to dropwise addition of 1.0 M lithium bis-(trimethylsilyl)amide (74 mL, 1.1 equiv). The reaction suspension was stirred at room temperature for 20 min prior to addition of sodium thiomethoxide (5.21 g, 74.2 mmol). The reaction solution was allowed to stir at reflux for 3 hr. The reaction was determined to be complete after quenching a reaction aliquot in dilute aq. HCl and running GCMS: found m/z=265, 267 parent ions. The cooled reaction mixture was quenched with H$_2$O and diluted with EtOAc (200 mL). The reaction mixture was transferred to a reparatory funnel, and 1.0 N aq. HCl was added to give a pH=2-3 solution. The ethyl acetate layer was separated, washed with brine, dried over Na$_2$SO$_4$, and concentrated in vacuo to afford 14.6 g (81% yield) of the intermediate 6-fluoro-4-bromo-2-methylsulfanyl-benzoic acid as a waxy white solid. $^1$H NMR (400 MHz, CDCl$_3$) δ 7.18 (s, 1H), 7.12 (dd, J=8 Hz, 1H), 2.49 (s, 3H); GCMS m/z=265, 267 [M]$^+$.

Alternatively, the intermediate 6-fluoro-4-bromo-2-methylsulfanyl-benzoic acid was prepared as follows:

To a 20 L flask was charged dimethyl formamide (14.5 L, 10.0 vol), followed by sodium hydroxide (293.7 g, 1.2 eq) and the reaction mass cooled to −15 to −10° C. 4-bromo-2,6-difluorobenzoic acid (1450 g, 1.0 equiv) was added over a period of 10-15 min at −15 to −10° C. and stirred for an additional 10-15 min. Sodium thiomethoxide (514.6 g, 1.2 equiv) was added over a period of 5-10 min at −10 to −5° C. On completion of the addition the temperature of the reaction was raised to 25-28° C. over a period of 45 to 60 min and maintained at that temperature 1.5-2 h. The temperature of the reaction was then raised to 60-65° C. over a period of 30-60 min and maintained at 60-65° C. for 5 h until the reaction was deemed complete. The reaction mixture was then cooled to 20-25° C. and quenched with a cooled (5-10° C.) solution of 2N HCl (5.045 L of 12N HCl in 30.3 L water). Following the quench, ethyl acetate (14.5 L, 10 vol) was added and the mixture stirred for 10-15 min. The phases were separated and the aqueous layer was extracted with ethyl acetate (7.25 L, 5 vol). The two phases were separated and the combined organic layer was washed with a brine solution (725 g of NaCl in 3.625 L of water). The phases were separated and the organic layer was washed with water (5.0 vol, 7.25 L). The phases were separated and the organic layer was dried over sodium sulfate (1450 g). The organic layer was filtered to remove the sodium sulfate, which was then washed with ethyl acetate (2.9 L, 2 vol). The organic layer was concentrated under reduced pressure at 45-50° C./30-40 mm Hg to ~1 to 1.2 volumes and petroleum ether (7.25 L, 5 vol) was added at 40-45° C. over a period of 15-20 min. The solution was cooled to 20-25° C. over a period of 20-25 min. The solid was filtered and washed with petroleum ether (2.9 L, 2.0 vol) and the product dried under vacuum at 25-28° C., 0.4 to 0.7 mbar to afford 1410 g (87%, 99.40 Area %) of the intermediate 6-fluoro-4-bromo-2-methylsulfanyl-benzoic acid.

Step 2b

Preparation of (4-bromo-2-fluoro-6-(methylthio)phenyl)methanol

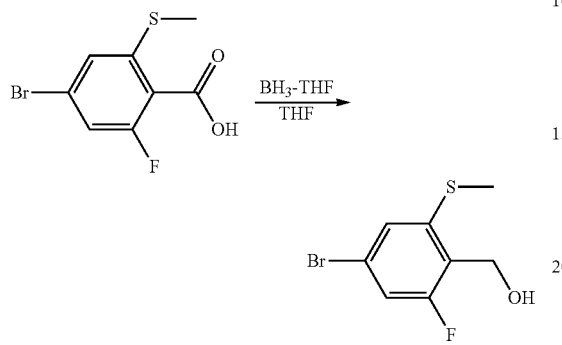

Into a $N_2$ purged 500 mL round bottom flask attached with condenser was added 6-fluoro-4-bromo-2-methylsulfanyl-benzoic acid (14.6 g, 55.0 mmol) and anhydrous THF (70 mL). The reaction solution was allowed to cool to 0° C. prior to dropwise addition of a 1.0 M $BH_3$-THF (83 mL, 1.5 equiv) solution in THF. The reaction solution was stirred at room temperature then at reflux for an additional 2 hr. The reaction solution was cooled prior to quenching with a 1:1 $H_2O$/THF solution. The reaction solution was transferred to a separatory funnel with EtOAc (100 mL) and an aqueous solution of $K_2CO_3$ was added. The ethyl acetate phase was separated, washed with brine, dried over $Na_2SO_4$, and concentrated in vacuo. The crude product was chromatographed through a 110 g $SiO_2$ column using a solvent gradient of 100% Hx to 55% EtOAc. The purified title product was obtained as a solid white wax (13.7 g, 99% yield). $^1$H NMR (400 MHz, $CDCl_3$) δ 7.13 (s, 1H), 7.06 (dd, $J_1$=8 Hz, $J_2$=2 Hz, 1H), 4.77 (s, 2H), 2.51 (s, 3H), 2.20-2.05 (br s, 1H); GCMS m/z=251, 253 [M]$^+$.

Alternatively, the intermediate (4-bromo-2-fluoro-6-(methylthio)phenyl)methanol was prepared as follows:

To a 20 L flask was charged 4-bromo-2-fluoro-6-(methylthio)benzoic acid (1400 g, 1.0 eq) followed by THF (14 L, 10 vol) under nitrogen. To this solution was added borane-dimethyl sulfide complex (802.41 g, 1000 mL) at 25-28° C. over a period of 30-45 min. The reaction temperature was raised to 60-65° C. over a period of 30-45 min and the temperature maintained until HPLC showed <1% of 4-bromo-2-fluoro-6-(methylthio)benzoic acid (~3-4 h). On completion of the reaction the mixture was cooled to 10-15° C. over a period of 30-40 min. The reaction was then quenched with methanol (2.1 L, 1.5 vol) over a period of 1 to 1½ h at 10-15° C. The reaction mass was then concentrated under vacuum at 40-50° C./0.4 to 0.7 mbar to 1 to 1.5 volumes. The resultant mixture was dissolved in DCM (8.4 L, 6 vol). The organic layer was washed with an ammonium chloride solution (560 g $NH_4Cl$ in 2.8 L water, 2 vol). The phases were separated and the organic layer was washed with 10% $NaHCO_3$ solution (2.8 L, 2 vol), saturated brine solution (2.1 L, 1.5 vol) and water (4.2 L, 3 vol). The organic layer was separated and dried over sodium sulfate (700 g). The sodium sulfate was removed by filtration and washed with DCM (2.8 L, 2 vol). The organic layer was concentrated under vacuum at 40-45° C./0.4 to 0.7 mbar to 1 to 1.2 vol to afford the product which was dried under vacuum at 45-50° C./0.4 to 0.7 mbar. The title product was obtained in 90% yield (1200 g) with 90.07 Area %.

Step 2c

Preparation of (4-bromo-2-fluoro-6-(methanesulfonyl)phenyl)-methanol

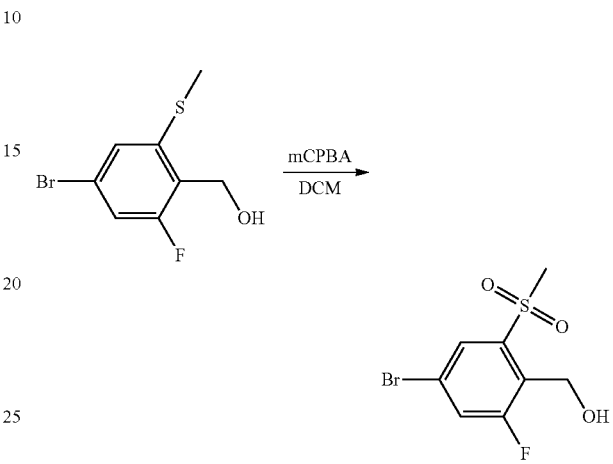

To a 500 mL flask was added (4-bromo-2-fluoro-6-(methylthio)phenyl)methanol (13.7 g, 54.6 mmol) and anhydrous dichloromethane (125 mL). The solution was cooled to 0-3° C. in an ice bath prior to portionwise addition of 3-chloroperbenzoic acid (77% max., Aldrich) (18.8 g, 2 equiv). The reaction solution was then allowed to warm to room temperature where it remained for 18 h. The reaction was then concentrated in vacuo to remove dichloromethane and the residue was washed into a separatory funnel with ethyl acetate and 1 M aq. NaOH. The ethyl acetate layer was separated, washed with 1 M aq. NaOH, dried over $Na_2SO_4$, and concentrated in vacuo. The residue was purified by flash chromatography (Biotage, 65×200 mm $SiO_2$ column, gradient elution from 100% hexanes to 90% ethyl acetate). Appropriate fractions were combined and concentrated in vacuo to afford the title compound as a colorless, semi-crystalline solid, yield: 8.1 g (52%). $^1$H NMR (400 MHz, DMSO-$d_6$) δ 7.98 (dd, J=8 Hz, 1H), 7.91 (s, 1H), 5.45 (t, J=8 Hz, 1H), 4.88 (dd, $J_1$=8 Hz, $J_2$=2 Hz, 2H), 3.42 (s, 3H); $^{19}$F NMR (400 MHz, DMSO-$d_6$) δ-111.8 ppm; GCMS m/z=283, 285 [M]$^+$.

Step 2d

Preparation of (2-fluoro-6-(methylsulfonyl)-4-(4,4,5,5-tetramethyl-1,3,2-dioxaborolan-2-yl)phenyl)methanol

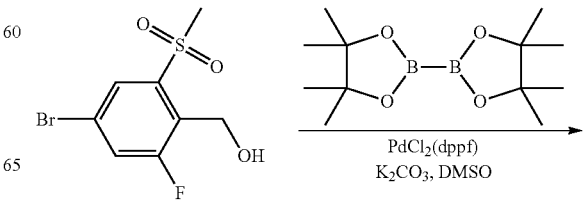

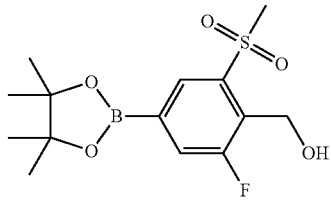

To a 100 mL round bottom flask, purged with dry N₂, was weighed (4-bromo-2-fluoro-6-(methanesulfonyl)phenyl)-methanol (1.98 g, 6.99 mmol), bis(pinacolato)diboron (2.13 g 1.2 equiv), dichloro[1,1'-bis(diphenylphosphino)ferrocene] palladium (II) dichloromethane adduct (560 mg, 10 mol %), potassium carbonate (2.06 g, 3 equiv), and DMSO (25 mL). The resulting suspension was allowed to stir at 90° C. for 3 h. An aliquot of reaction solution was found to contain no more starting bromide as determined by LCMS analysis. The cooled reaction suspension was diluted with ethyl acetate (50 mL) and water (50 mL) and filtered through a Celite padded Buchner Funnel. The resulting filtrate was transferred to a separatory funnel, and the organic phase was separated. The aqueous phase was extracted with ethyl acetate, and the combined ethyl acetate phases were washed with brine, dried over Na₂SO₄, and concentrated in vacuo. The residue was purified by silica gel flash chromatography (Biotage SP-1, 40 g SiO₂ column, gradient elution from 100% hexanes to 60% ethyl acetate) to afford a clear viscous oil. The product was isolated as an amorphous white powder by dissolving in dichloromethane and reprecipitation resulted upon addition of hexanes. The title compound was isolated as a solid white powder, yield: 1.9 g (82% yield). ¹H NMR (400 MHz, CDCl₃) δ 8.28 (s, 1H), 7.79 (d, J=8 Hz, 1H), 5.03 (d, J=8 Hz, 2H), 3.23 (s, 3H) 3.05 (t, J=8 Hz, 1H), 1.35 (s, 6H); ¹⁹F NMR (400 MHz, CDCl₃) δ-116.3 ppm.

Alternatively, the intermediate (2-fluoro-6-(methylsulfonyl)-4-(4,4,5,5-tetramethyl-1,3,2-dioxaborolan-2-yl)phenyl)methanol was prepared as follows:

To a 500 mL jacketed reactor equipped with a stir bar, temperature probe, reflux condenser and a nitrogen inlet was charged methyl tetrahydroran (MeTHF) (75 mL, 5 volumes) followed by potassium acetate (5.2 g, 52.98 mmoles, 1 equiv.) and (oxydi-2,1-phenylene)bis(diphenylphosphine) (322 mg; 597.3 μmoles, 0.01125 equiv.) and bis(pinacolato)diboron (17.51 g, 68.95 mmoles, 1.3 equiv.). The reaction flask was evacuated to less than 150 Torr, and then back filled with nitrogen. This degassing procedure was repeated 3 times. Pd(OAc)₂ (94.2 mg; 419.6 μmoles, 0.0075 equiv.) was charged to the reactor and the reaction flask was evacuated to less than 150 Torr, and then back filled with nitrogen and the sequence repeated 3 times. The resulting slurry was allowed to age at 20-25° C. for 15 min. Upon completion of the 15 min age, the slurry was heated to an internal temperature of 80° C. As the mixture in the reactor was heating to temperature, in a separate flask was charged (4-bromo-2-fluoro-6-(methanesulfonyl)phenyl)-methanol (15.03 g, 53.09 mmoles, 1 equiv.) followed by MeTHF (75 ml, 5 volumes). The resulting solution was degassed by bubbling nitrogen subsurface for at least 15 min. prior to use. Once the catalyst mixture had reached reflux, the degassed solution of (4-bromo-2-fluoro-6-(methanesulfonyl)phenyl)-methanol in MeTHF was added to the reaction in a single portion and allowed to react. The reaction typically takes ~20 hours to complete after the addition of substrate. Upon completion (typically <0.75 RAP of starting material the reaction was cooled to 20-25° C. Once at RT the reaction was diluted with MeTHF (75 ml, 5 volumes) and washed with a 5 wt % NaCl solution (7.5 volumes, 110 ml) for at least 15 min. The phases were separated and the upper product rich MeTHF stream was filtered through Celite to remove insoluble palladium residues. The Celite cake was washed with MeTHF (75 ml, 5 volumes). The reaction was treated with functionalized silica (30 equiv) to remove palladium and color. The slurry was agitated for at least 60 min and then filtered to remove the silica. The used silica was washed with MeTHF (5 volumes, 75 ml). The combined organic phase was washed with water (5 volumes, 75 ml). The organic was distilled to 5 volumes (75 ml) under vacuum (60-70 Torr, bath temp of 30° C.). When the 75 ml landmark was reached the distillation was stopped and heptane (75 ml, 5 volumes) was added drop wise to the reaction solution. After ~35 ml of heptanes had been added the product began to crystallize from the solution. On completion of the addition the product was isolated by filtration and the wet cake washed with MeTHF-heptanes (1:9) solution (2×75 ml) and dried at 50° C. The title product was obtained a white solid, 13.64 g, (78% yield) with 99.58 Area %.

Example 1

2-(1-(3-chloro-3'-fluoro-4'-(hydroxymethyl)-5'-(methylsulfonyl)biphenyl-4-yl)-2-(2-(2-fluorophenyl)propan-2-yl)-1H-imidazol-4-yl)propan-2-ol

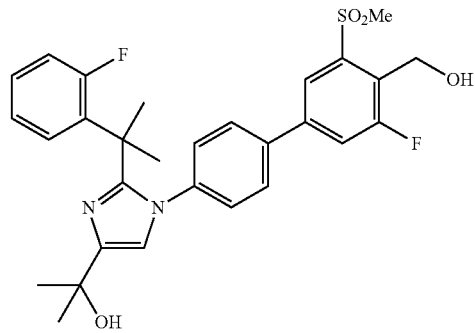 [SMILES: CC(C)(O)c1cn(-c2ccc(-c3cc(F)c(CO)c(S(C)(=O)=O)c3)cc2)c(C(C)(C)c2ccccc2F)n1]

Example 1a

Preparation of 2-(2-fluorophenyl)-2-methylpropanenitrile

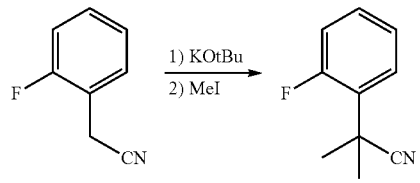

To a 500 mL 3-neck round bottom flask with an attached addition funnel that has been purged with dry N₂, was added 2-fluorophenylacetonitrile (11.0 g, 81.4 mmol) and anhydrous THF (70 mL). The reaction solution was cooled to −10° C. prior to dropwise addition of a 1.0 M potassium tert-butoxide solution (195 mL, 2.4 molar equiv) in THF. The reaction solution was stirred at −10° C. for 20 min prior to addition of iodomethane (15.2 mL, 244 mmol). The reaction solution was allowed to stir warming to room temperature for 4 hr. The reaction solution was quenched by addition of aq NH$_4$Cl and diluted with EtOAc (200 mL). The organic phase was partitioned, washed with aq NH$_4$Cl, dried over Na$_2$SO$_4$, filtered, concentrated in vacuo and chromatographed through a 240 g SiO$_2$ column on the Biotage SP-1 using a solvent gradient of 100% Hx to 50% EtOAc to afford 10.1 g (76% yield) of title product. GCMS m/z=163 [M]$^+$.

Example 1b

Preparation of N-(4-bromophenyl)-2-(2-fluorophenyl)-2-methylpropanimidamide

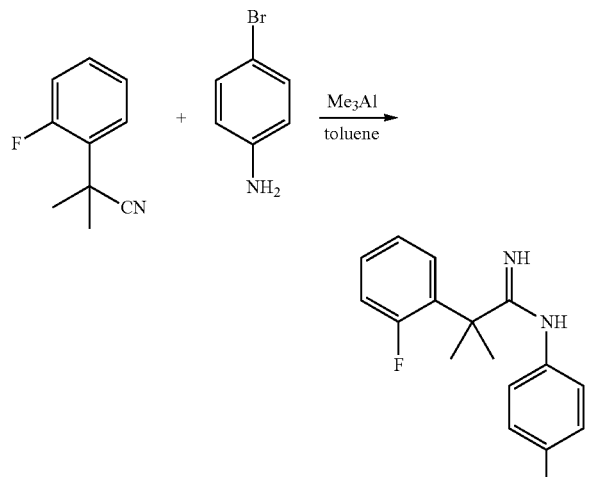

To an oven dried, N$_2$ purged 250 mL round bottom flask attached with addition funnel was added 4-bromoaniline (7.31 g, 42.5 mmol) and anhydrous toluene (40 mL). To the reaction solution at 0° C. was added a 2.0 M Me$_3$Al (32 mL, 1.5 molar equiv) solution. The reaction solution was stirred at 0° C. for 30 min, then a solution of 2-(2-fluorophenyl)-2-methylpropanenitrile (7.62 g, 46.7 mmol) in toluene (25 mL) was added to the reaction flask. The reaction solution was allowed to stir at 90° C. for 5 hr. The cooled reaction solution was quenched with an aq sodium potassium tartrate solution. After standing 20 min, the organic phase was partitioned and washed with sodium potassium tartrate solution. The organic solution was extracted with 1N aq HCl (100 mL×3). The combined aq HCl solution was neutralized by addition of 1N aq NaOH and extracted with dichloromethane (200 mL×2). The dichloromethane product solution was dried over Na$_2$SO$_4$, filtered, and concentrated in vacuo to afford the title compound (5.5 g, 39% yield). GCMS m/z=334, 336 [M]$^+$.

Example 1c

Preparation of ethyl 1-(4-bromophenyl)-2-(2-(2-fluorophenyl)propan-2-yl)-1H-imidazole-4-carboxylate

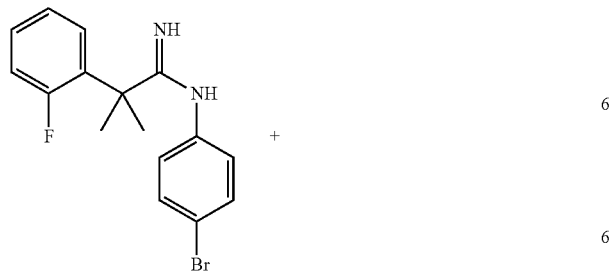

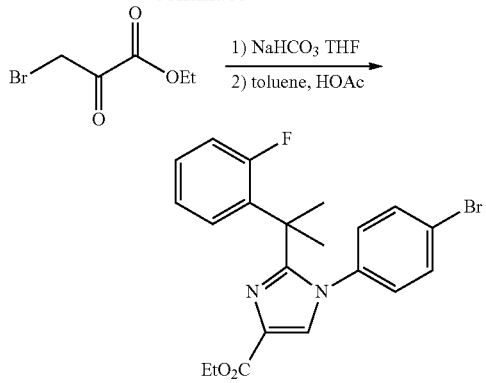

To a 250 mL round bottom flask attached with condenser was added N-(4-bromophenyl)-2-(2-fluorophenyl)-2-methylpropanimidamide (5.0 g, 15 mmol), anhydrous THF (80 mL), NaHCO$_3$ (2.52 g, 30 mmol), and 90% ethyl bromopyruvate (1.90 mL, 15.1 mmol). The reaction mixture was stirred at 70° C. for 2 hr prior to analysis by LCMS. The cooled reaction mixture was decanted and concentrated in vacuo. The residue was taken into toluene (65 mL) and acetic acid (1.8 mL). The solution was stirred at reflux for 1 hr. The cooled solution was washed with H$_2$O (150 mL×3), dried over Na$_2$SO$_4$, filtered, concentrated in vacuo, and chromatographed through a SiO$_2$ column using a 100% Hx to 70% EtOAc gradient to afford purified title compound (4.3 g, 67% yield). LCMS (ES): m/z=431.3, 433.3 [M+H]$^+$.

Example 1d

Preparation of 2-(1-(4-bromophenyl)-2-(2-(2-fluorophenyl)propan-2-yl)-1H-imidazol-4-yl)propan-2-ol

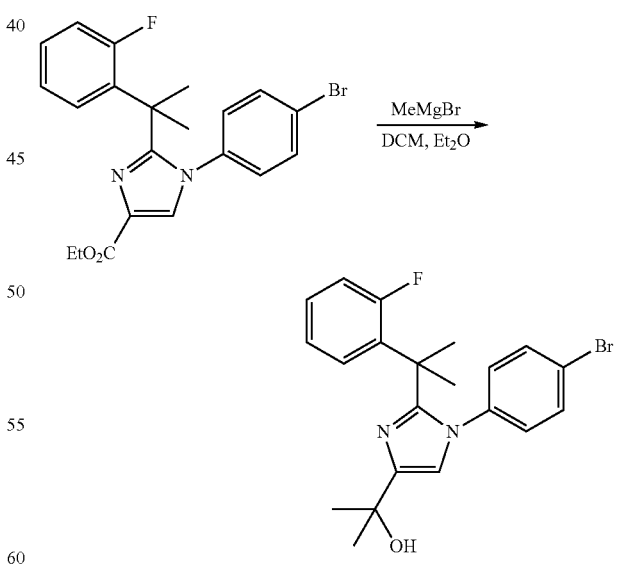

To a 250 mL round bottom flask, purged with dry N$_2$ and attached with addition funnel, was added a 3.0M MeMgBr (12 mL, 3.7 equiv) solution in Et$_2$O. The flask was cooled to 0° C. prior to dropwise addition of ethyl 1-(4-bromophenyl)-2-(2-(2-fluorophenyl)propan-2-yl)-1H-imidazole-4-carboxylate (4.22 g, 9.78 mmol) in a solution of anhydrous dichloromethane (80 mL). The reaction solution was allowed to stir, warming to room temperature over 1 hr. The reaction solution was quenched by addition of aq NH$_4$Cl. The mixture was poured to a reparatory funnel and the dichloromethane layer was partitioned, dried over Na$_2$SO$_4$, filtered, concentrated and chromatographed through a 40 g SiO$_2$ column using a gradient of 100% Hx to 70% EtOAc to yield the title compound (3.19 g, 78% yield). LCMS (ES): m/z=417.3, 419.3 [M+H]$^+$.

Example 1

Preparation of 2-(1-(3'-fluoro-4'-(hydroxymethyl)-5'-(methylsulfonyl)biphenyl-4-yl)-2-(2-(2-fluorophenyl)propan-2-yl)-1H-imidazol-4-yl)propan-2-ol

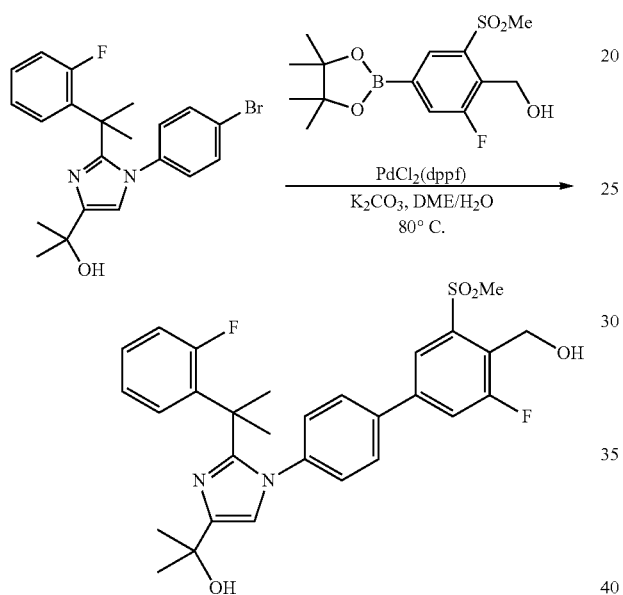

To a 50 mL round bottom flask was added 2-(1-(4-bromophenyl)-2-(2-(2-fluorophenyl)propan-2-yl)-1H-imidazol-4-yl)propan-2-ol (380 mg, 911 µmol), DME (25 mL) and H$_2$O (6 mL). The solution was sparged with N$_2$ for 10 min prior to addition of (2-fluoro-6-(methylsulfonyl)-4-(4,4,5,5-tetramethyl-1,3,2-dioxaborolan-2-yl)phenyl)methanol (360 mg, 1.09 mmol), potassium carbonate (380 mg, 2.73 mmol), and dichloro[1,1'-bis(diphenylphosphino)ferrocene]palladium (II) dichloromethane adduct (74 mg, 91 µmol). The reaction mixture was allowed to stir at 80° C. for 2 h. The cooled reaction solution was diluted with EtOAc (30 mL) and filtered through a Celite padded Buchner funnel. The filtrate was washed with aq NH$_4$Cl (150 mL×2). The organic phase was dried over Na$_2$SO$_4$, filtered, and concentrated in vacuo. The residue was purified by silica gel flash chromatography (Biotage SP-1, 25 g SiO$_2$ column, gradient elution from 5% EtOAc to 100% EtOAc) to afford the title compound (100 mg, 20% yield). $^1$H-NMR (400 MHz, CDCl$_3$) δ 8.02 (d, J=2 Hz, 1H), 7.51 (dd, J$_1$=2 Hz, J$_2$=10 Hz, 1H), 7.29 (d, J=9 2H), 7.08-7.16 (mult, 1H), 6.85-6.92 (mult, 3H), 6.77-6.84 (mult, 2H), 6.65 (s, 1H), 5.09 (d, J=6 Hz, 2H), 3.35 (s, 1H), 3.30 (2, 3H), 3.02 (t, J=6 Hz, 1H), 1.72 (s, 6H), 1.62 (s, 6H); $^{19}$F NMR (400 MHz, CDCl$_3$) δ−112.1, −113.5 ppm; LCMS (ES) m/z=541.3 [M+H]$^+$, 563.2 [M+Na]$^+$.

Examples 2-8

All of the following compounds were made in a similar manner to that described in Example 1 using appropriate anilines and 2-(phenyl)-2-methylpropanenitriles. If not commercially available, nitriles were made using standard techniques that are readily apparent to one skilled in the art.

| No. | Name | Structure | Data |
|---|---|---|---|
| 2 | 2-(2-(2-(2-chloro-6-fluorophenyl)propan-2-yl)-1-(3'-fluoro-4'-(hydroxymethyl)-3-methyl-5'-(methylsulfonyl)biphenyl-4-yl)-1H-imidazol-4-yl)propan-2-ol | 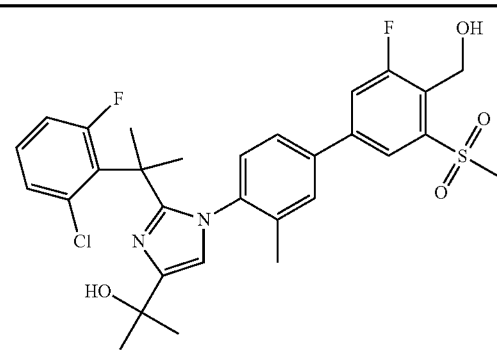 | MS (ES): 589.3 [M + H]$^+$ |

| No. | Name | Structure | Data |
|---|---|---|---|
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol | 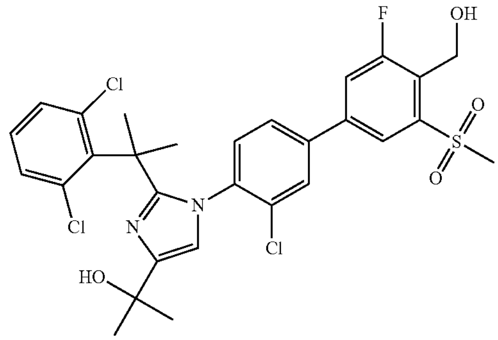 [SMILES: CC(C)(O)c1cn(-c2ccc(-c3cc(F)c(CO)c(S(C)(=O)=O)c3)cc2Cl)c(C(C)(C)c2c(Cl)cccc2Cl)n1] | MS (ES): 627.2 [M + H]+ |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol | 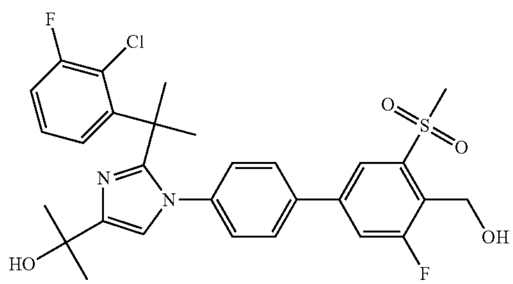 [SMILES: CC(C)(O)c1cn(-c2ccc(-c3cc(F)c(CO)c(S(C)(=O)=O)c3)cc2)c(C(C)(C)c2cccc(F)c2Cl)n1] | MS (ES): 575.3 [M + H]+ |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol | 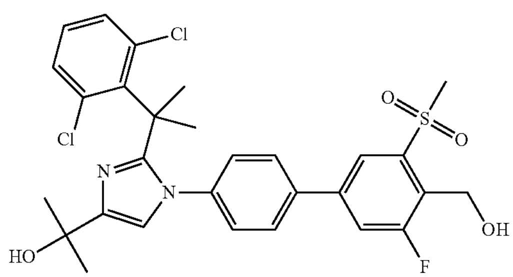 [SMILES: CC(C)(O)c1cn(-c2ccc(-c3cc(F)c(CO)c(S(C)(=O)=O)c3)cc2)c(C(C)(C)c2c(Cl)cccc2Cl)n1] | MS (ES): 591.5 [M + H]+ |
| 6 | 2-(2-(2-(2-Chloro-phenyl)propan-2-yl)-1-(3,3'-difluoro-4'-hydroxymethyl-5'-(methylsulfonyl)biphenyl-4-yl)-1H-imidazol-4-yl)-propan-2-ol | 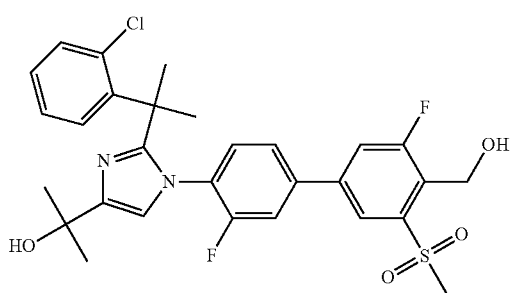 | MS (ES): 575.3 [M + H]+ |
| 7 | 2-(2-(2-(2-chloro-6-fluorophenyl)propan-2-yl)-1-(3,3'-difluoro-4'-(hydroxymethyl)-5'-(methylsulfonyl)biphenyl-4-yl)-1H-imidazol-4-yl)propan-2-ol | 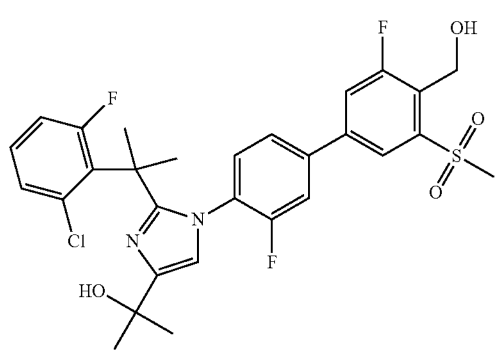 | MS (ES) 593.3, 595.3 [M + H]+ |

US 8,618,154 B2

| No. | Name | Structure | Data |
|---|---|---|---|
| 8 | 2-{1-(3,3'-Difluoro-4'-hydroxymethyl-5'-methanesulfonyl-biphenyl-4-yl)-2-[2-(2-fluorophenyl)propan-2-yl]-1H-imidazol-4-yl}-propan-2-ol | 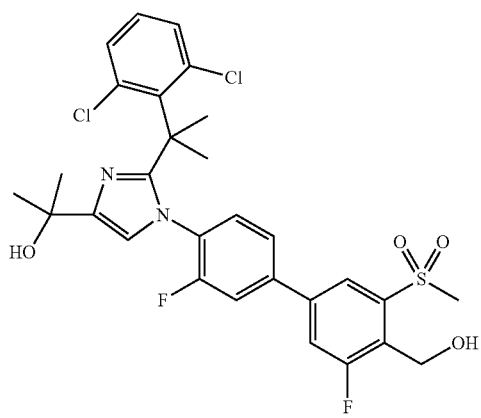 | MS (ES): 559.2 [M + H]+ |

Compound 2 has the following NMR characteristics: 1H NMR (400 MHz, CDCl$_3$) δ 8.02 (s, 1H), 7.56-7.49 (m, 1H), 7.35 (d, J=2.0, 1H), 7.12-6.96 (m, 3H), 6.68 (d, J=8.2, 1H), 6.66-6.60 (m, 1H), 6.56 (s, 1H), 5.08 (d, J=5.4, 2H), 3.36 (s, 1H), 3.29 (s, 3H), 2.92 (t, J=7.0, 1H), 2.07 (s, 3H), 1.97 (d, J=2.4, 3H), 1.72 (d, J=7.4, 3H), 1.59 (s, 6H).

Compound 3 has the following NMR characteristics: 1H NMR (400 MHz, CDCl$_3$) δ 8.00 (m, 1H), 7.57 (d, J=2.1, 1H), 7.55-7.49 (m, 1H), 7.13 (s, 1H), 7.11 (s, 1H), 7.07 (dd, J=8.3, 2.1, 1H), 7.01-6.95 (m, 1H), 6.81 (d, J=8.3, 1H), 6.59 (s, 1H), 5.09 (d, J=5.4, 2H), 3.30 (s, 3H), 3.26 (m, 1H), 2.89 (t, J=7.0, 1H), 2.06 (s, 3H), 1.92 (s, 3H), 1.61 (s, 3H), 1.59 (s, 3H).

Compound 4 has the following NMR characteristics: 1H NMR (400 MHz, CDCl$_3$) δ 7.97 (s, 1H), 7.47 (dd, J=10.0, 1.8, 1H), 7.31-7.20 (m, 2H), 7.00 (d, J=8.3, 2H), 6.92-6.71 (m, 3H), 6.65 (s, 1H), 5.08 (dd, J=7.0, 1.6, 2H), 3.29 (s, 3H), 3.27 (s, 1H), 2.90 (t, J=7.0, 1H), 1.82 (s, 6H), 1.60 (s, 6H).

Compound 5 has the following NMR characteristics: 1H-NMR (400 MHz, DMSO-d6) δ 7.89-7.90 (mult, 1H), 7.82-7.85 (mult, 1H), 7.52 (d, J=8.6 Hz, 2H), 7.16 (d, J=8.6 Hz 2H), 7.07-7.09 (mult, 2H), 6.94-6.98 (mult, 1H), 6.80 (s, 1H), 5.55 (t, J=5.2 Hz, 1H), 4.93-4.95 (mult, 2H), 4.65 (s, 1H), 3.45 (s, 3H), 1.96 (s, 6H), 1.45 (s, 6H).

Compound 6 has the following NMR characteristics: 1H NMR (400 MHz, CDCl$_3$) δ 7.97 (s, 1H), 7.46 (dd, J=9.9, 1.8, 1H), 7.23-7.18 (m, 1H), 7.12 (dd, J=10.3, 1.9, 1H), 6.97 (ddd, J=23.4, 9.0, 4.0, 2H), 6.88-6.79 (m, 2H), 6.61 (s, 1H), 5.08 (d, J=5.4, 2H), 3.30 (s, 3H), 3.27-3.23 (m, 1H), 2.92 (t, J=6.9, 1H), 1.61 (s, 12H).

Compound 7 has the following NMR characteristics: 1H-NMR (DMSO-d6, 400 MHz) δ 7.95-7.90 (m, 2H), 7.62 (dd, 1H, J=11, 1.5 Hz), 7.33 (dd, 1H, J=9.5, 1.5 Hz), 7.13-7.08 (m, 3H), 6.85 (s, 1H), 6.80-6.70 (m, 1H), 5.57 (t, 1H, J=5.3 Hz), 4.95 (d, 2H, J=4.3 Hz), 4.71 (s, 1H), 3.47 (s, 3H), 1.85 (s, 6H), 1.46 (s, 6H).

Compound 8 has the following NMR characteristics: 1H-NMR (DMSO-d6, 400 MHz) δ 7.96-7.90 (m, 2H), 7.49 (dd, 1H, J=11, 1.5 Hz), 7.34 (dd, 1H, J=9.5, 1.5 Hz), 7.20-7.10 (m, 1H), 7.05-6.94 (m, 2H), 6.90-6.75 (m, 3H), 5.57 (t, 1H, J=5.3 Hz), 4.94 (d, 2H, J=4.3 Hz), 4.70 (s, 1H), 3.47 (s, 3H), 1.68 (s, 6H), 1.47 (s, 6H).

Example 9

2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol

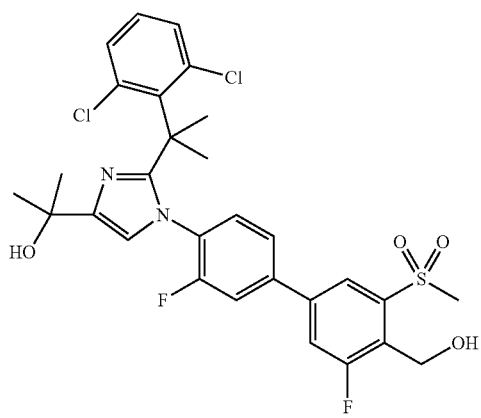 [SMILES: CC(C)(O)c1cn(-c2ccc(-c3cc(F)c(CO)c(S(C)(=O)=O)c3)cc2F)c(C(C)(C)c2c(Cl)cccc2Cl)n1]

Example 9a

Preparation of
2-(2,6-dichlorophenyl)-2-methylpropanenitrile

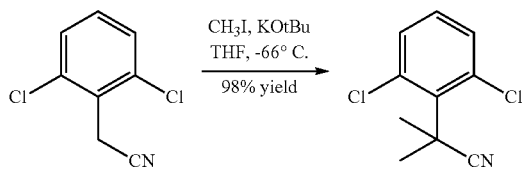

To a 1 M solution of potassium tert-butoxide (403 mL, 403 mmol) at −66° C. (acetone/dry ice) was slowly added 2-(2,6-dichlorophenyl)acetonitrile (25.0 g, 134 mmol) in anhydrous THF (150 mL). The mixture was stirred at −66° C. for 20 minutes. Then, iodomethane (33.6 mL, 538 mmol) was added drop-wise over 25 minutes at −66° C. At this stage, it was exothermic and a large amount of light yellow precipitate was observed. The suspension was stirred at −60° C. for 30 minutes. The reaction mixture was quenched with 200 mL ice water, and extracted with ether (3×150 mL). The organics were combined, washed with 150 mL brine, dried over Na₂SO₄, and concentrated on a rotary evaporator. The crude product (30 g, yellow oil) was purified by column chromatography (ISCO, 330 g silica, 20% EtOAc in hexanes) to afford 2-(2,6-dichlorophenyl)-2-methylpropanenitrile (28.2 g, 132 mmol, 98% yield) as a light yellowish oil. ¹H-NMR (CDCl₃, 400 MHz) δ 7.35 (d, 2H, J=8.03 Hz), 7.16 (t, 1H, J=8.0 Hz), 2.09 (s, 6H); ¹³C-NMR (CDCl₃, 126 MHz) δ134.6, 133.8, 131.4, 129.0, 124.1, 38.6, 29.2; MS m/e 214.10 (M+H⁺); HPLC (XBridge 5μ C18 4.6×50 mm, 4 mL/min, Solvent A: 10% MeOH/water with 0.2% H₃PO₄, Solvent B: 90% MeOH/water with 0.2% H₃PO₄, gradient with 0-100% B over 4 minutes): 3.16 minutes.

Example 9b

Preparation of N-(4-bromo-2-fluorophenyl)-2-(2,6-dichlorophenyl)-2-methylpropanimidamide

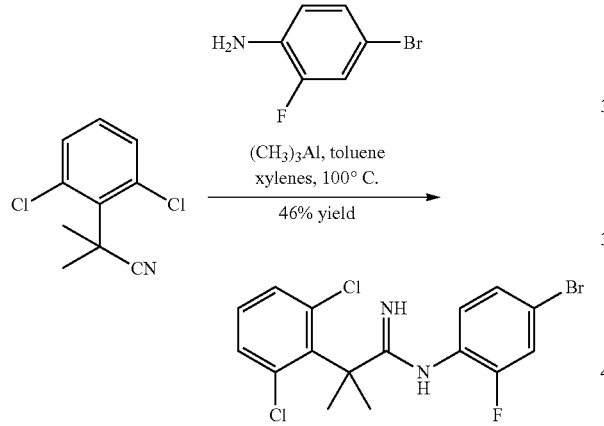

2-(2,6-Dichlorophenyl)-2-methylpropanenitrile (20 g, 93 mmol) and 4-bromo-2-fluoroaniline (28.4 g, 149 mmol) were dissolved in anhydrous o-xylene (200 mL) and heated to 100° C. under N₂. Trimethylaluminum (2 M) in toluene (140 mL, 280 mmol) was added drop-wise (~0.9 mL per minute) over 2.5 hours while the reaction mixture was stirred at 100° C. After addition, the reaction mixture was stirred at 100° C. for 30 minutes, and then cooled to −5° C. The reaction mixture was very carefully quenched with potassium sodium tartrate (20 g in 100 mL water) (Caution: gas and heat formation). The reaction mixture was filtered through Celite 545. The filtrate was washed with 1N HCl (4×70 mL). The aqueous was neutralized with 2N NaOH and extracted with EtOAc (4×100 mL). The organics were combined, washed with brine, dried with Na₂SO₄, and concentrated on a rotary evaporator to afford 24 g of crude product. The crude product was recrystallized with 72 mL of MTBE and 240 mL of hexane to give N-(4-bromo-2-fluorophenyl)-2-(2,6-dichlorophenyl)-2-methylpropanimidamide (17.5 g, 43.3 mmol, 46.4% yield) as a white solid (purity: 99%). ¹H-NMR (MeOD, 400 MHz) δ 7.42 (d, 2H, J=8.0 Hz), 7.30 (m, 2H), 7.16 (t, 1H, J=8.0 Hz), 6.93 (t, 1H, J=8.0 Hz), 2.11 (s, 6H); ¹³C-NMR (DMSO-d₆, 100 MHz) δ 166.5, 156.1, 153.7, 140.6, 138.5, 135.9, 131.4, 128.6, 128.0, 125.7, 119.5, 112.9, 50.0, 29.2; MS m/e 403.09 (M+H⁺); HPLC (XBridge 5μ C18 4.6×50 mm, 4 mL/min, Solvent A: 10% MeOH/water with 0.2% H₃PO₄, Solvent B: 90% MeOH/water with 0.2% H₃PO₄, gradient with 0-100% B over 4 minutes): 2.32 minutes.

Example 9c

Preparation of ethyl 1-(4-bromo-2-fluorophenyl)-2-(2-(2,6-dichlorophenyl)propan-2-yl)-4-hydroxy-4,5-dihydro-1H-imidazole-4-carboxylate To a mixture of N-(4-bromo-2-fluorophenyl)-2-(2,6-dichlorophenyl)-2-methylpropanimidamide (48.0 g, 119 mmol), K₂CO₃ (41.0 g, 297 mmol) in toluene (180 mL) and THF (180 mL) at 55° C. was added slowly a solution of ethyl 3-bromo-2-oxopropanoate (23.3 mL, 166 mmol) in 24 mL of THF over 50 minutes. The reaction mixture was kept at 55° C. for 1.5 hours. A white slurry was observed. The reaction mixture was cooled to 5° C. HCl (0.5N, 450 mL) was added drop-wise (end point pH=9~10). After addition, the suspension was cooled to 0° C. The solid was collected by filtration, washed with water (2×50 mL), and then dried in a vacuum oven at 60° C. overnight. Ethyl 1-(4-bromo-2-fluorophenyl)-2-(2-(2,6-dichlorophenyl)propan-2-yl)-4-hydroxy-4,5-dihydro-1H-imidazole-4-carboxylate (59 g, 114 mmol, 96% yield) was obtained as a white solid. ¹H-NMR (CDCl₃, 400 MHz) δ 7.11 (m, 3H), 6.96 (m, 2H), 6.72 (t, 1H, J=8.28 Hz), 4.35 (m, 2H), 4.25 (d, 1H, J=10.5 Hz), 3.80 (d, 1H, J=10.8 Hz), 1.98 (s, 3H), 1.93 (s, 3H), 1.38 (t, 3H, J=7.03 Hz); ¹³C-NMR (CDCl₃, 126 MHz) δ 173.0, 171.5, 159.8, 157.8, 137.3, 135.7, 132.1, 131.1, 128.1, 127.4, 125.6, 122.2, 120.1, 93.5, 62.5, 45.5, 30.2, 14.0; MS m/e 517.05 (M+H⁺); HPLC (XBridge 5μ C18 4.6×50 mm, 4 mL/min, Solvent A: 10% MeOH/water with 0.2% H₃PO₄, Solvent B: 90% MeOH/water with 0.2% H₃PO₄, gradient with 0-100% B over 4 minutes): 2.74 minutes.

Example 9d

Preparation of ethyl 1-(4-bromo-2-fluorophenyl)-2-(2-(2,6-dichlorophenyl)propan-2-yl)-1H-imidazole-4-carboxylate

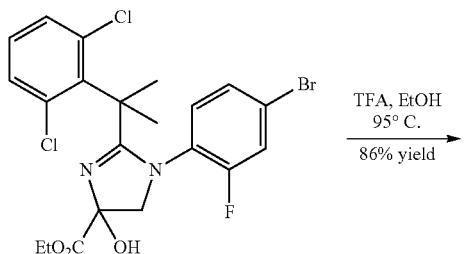

TFA, EtOH
95° C.
86% yield

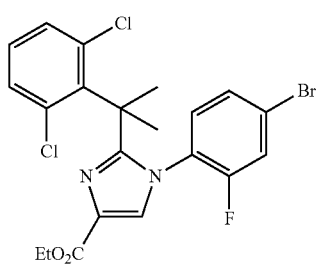

To a mixture of ethyl 1-(4-bromo-2-fluorophenyl)-2-(2-(2,6-dichlorophenyl)propan-2-yl)-4-hydroxy-4,5-dihydro-1H-imidazole-4-carboxylate (38 g, 73 mmol) in EtOH (200 mL) was added TFA (25.0 g, 220 mmol). The mixture was subsequently heated to 95° C. HPLC analysis after 2.5 hours showed <1% of alcohol intermediate remaining The mixture was diluted with 300 mL of $CH_2Cl_2$ and cooled to approximately 5° C. with an ice bath. The mixture was neutralized with 1N NaOH (120 mL) and the organic layer was separated. The aqueous layer was extracted with $CH_2Cl_2$ (2×100 mL). The combined organic layers were concentrated on a rotary evaporator to give crude material. Recrystallization in EtOH (5 mL/1 g) provided 32 g of ethyl 1-(4-bromo-2-fluorophenyl)-2-(2-(2,6-dichlorophenyl)propan-2-yl)-1H-imidazole-4-carboxylate as an off-white solid (86% yield). $^1$H-NMR (DMSO-$d_6$, 400 MHz) δ 7.92 (s, 1H), 7.16 (d, 1H, J=8.0 Hz), 7.22 (m, 3H), 7.11 (m, 1H), 7.04 (t, 1H, J=12.0 Hz), 4.25 (q, 2H, J=8.0 Hz), 1.94 (s, 6H), 1.27 (t, 3H, J=8.0 Hz); MS m/e 502.68 (M+H$^+$); HPLC (XBridge 5μ C18 4.6×50 mm, 4 mL/min, Solvent A: 10% MeOH/water with 0.2% $H_3PO_4$, Solvent B: 90% MeOH/water with 0.2% $H_3PO_4$, gradient with 0-100% B over 4 minutes): 3.87 minutes.

Example 9e

Preparation of 2-(1-(4-bromo-2-fluorophenyl)-2-(2-(2,6-dichlorophenyl)propan-2-yl)-1H-imidazol-4-yl)propan-2-ol

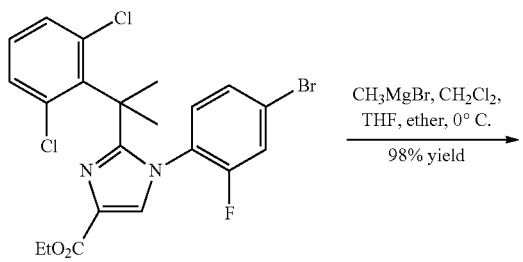

CH$_3$MgBr, CH$_2$Cl$_2$,
THF, ether, 0° C.
98% yield

-continued

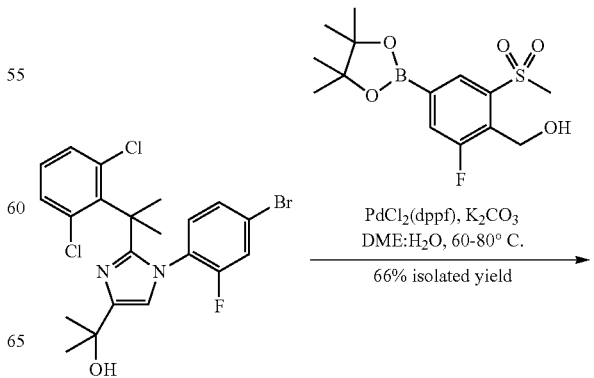

To a mixture of methylmagnesium bromide (60.0 mL, 180 mmol, 3M in ether) in 120 ml, of THF cooled with an ice/salt bath (−15 to −17° C.) was added slowly a solution of ethyl 1-(4-bromo-2-fluorophenyl)-2-(2-(2,6-dichlorophenyl)propan-2-yl)-1H-imidazole-4-carboxylate (30 g, 60 mmol) in 65 mL of $CH_2Cl_2$ and 87 mL of THF over 45 minutes. The internal temperature was carefully kept below 0° C. A further 2×20 mL of $CH_2Cl_2$ was used to wash forward the residual material. The reaction mixture temperature was maintained below 0° C. for 1 hour with stirring. Then the reaction mixture was diluted with 100 mL of $CH_2Cl_2$, and saturated $NH_4Cl$ was added slowly. The resulting mixture was extracted with $CH_2Cl_2$ (2×80 mL). Organics were combined, washed with brine, dried with $Na_2SO_4$, and concentrated on a rotary evaporator to afford 2-(1-(4-bromo-2-fluorophenyl)-2-(2-(2,6-dichlorophenyl)propan-2-yl)-1H-imidazol-4-yl)propan-2-ol (28.5 g, 58.6 mmol, 98% yield) as a white solid. $^1$H-NMR (CDCl$_3$, 400 MHz) δ 7.13 (dd, 1H, J=9.03, 2.01 Hz), 7.09 (s, 1H), 7.07 (s, 1H), 6.93 (m, 2H), 6.75 (t, 1H, J=8.16 Hz), 6.55 (s, 1H), 3.18 (s, 1H), 2.00 (s, 6H), 1.58 (s, 6H); $^{13}$C-NMR (CDCl$_3$, 126 MHz) δ 158.1, 156.1, 154.5, 147.8, 139.3, 135.7, 131.3, 130.3, 127.8, 126.9, 122.7, 119.8, 115.1, 68.7, 44.8, 31.1, 29.9; MS m/e 485.05 (M+H$^+$); HPLC (XBridge 5μ C18 4.6×50 mm, 4 mL/min, Solvent A: 10% MeOH/water with 0.2% $H_3PO_4$, Solvent B: 90% MeOH/water with 0.2% $H_3PO_4$, gradient with 0-100% B over 4 minutes): 2.78 minutes.

Example 9

Preparation of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol PdCl$_2$(dppf), K$_2$CO$_3$
DME:H$_2$O, 60-80° C.
66% isolated yield

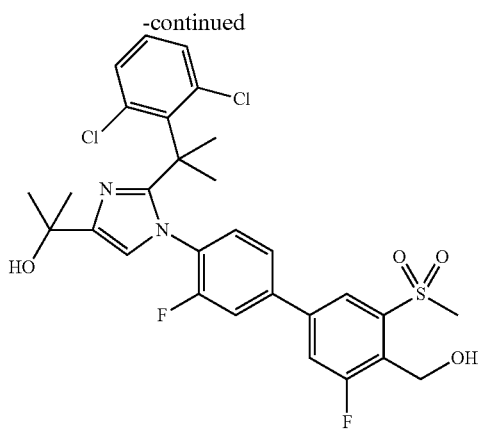

To a 1 L 3-necked round bottom flask under nitrogen was added 2-(1-(4-bromo-2-fluorophenyl)-2-(2-(2,6-dichlorophenyl)propan-2-yl)-1H-imidazol-4-yl)propan-2-ol (12.0 g, 24.7 mmol), [2-fluoro-6-methanesulfonyl-4-(4,4,5,5-tetramethyl-[1,3,2]dioxaborolan-2-yl)-phenyl]-methanol (9.78 g, 29.6 mmol), $K_2CO_3$ (10.2 g, 74 mmol), DME (120 mL) and water (12 mL). The mixture was heated to 60° C., and then 1,1'-bis(diphenylphosphino)ferrocene palladium (II) chloride complex (4.06 g, 4.94 mmol) was added under nitrogen. The reaction mixture was heated to 80° C. for 30 minutes. The resulting darkly colored mixture was cooled with an ice bath, and partitioned in 200 mL of $CH_2Cl_2$ and 200 mL of water. The organic layers were combined and dried with $Na_2SO_4$. After concentration, the crude product was purified by flash chromatography (ISCO, 330 g silica, 0% to 100% EtOAc in hexanes) to afford 12.79 g of crude product (85% yield) as a light yellow solid.

Recrystallization was carried out by dissolving 9.5 g of crude product in acetone (80 mL) at 65° C. The resulting solution was cooled slowly to 25° C. over 5 hours, and then cooled to 0° C. for an additional 30 minutes. Crystals began to form at 45° C. The solid was collected by filtration and rinsed with cold acetone. After drying in an oven at 45° C. under vacuum for 14 hours, 4.9 g of pure product was obtained. To recover additional crystalline product, the mother liquid was concentrated to approximately 10 mL and passed through a silica pad. EtOAc (100 mL) was used to elute the compound. The filtrate was concentrated under vacuum to give a crude solid. The crude solid was recrystallized in acetone following the procedure above to afford an additional 2.5 g of product. The combined recovery for the two crops after recrystallization was a 78% yield. $^1$H-NMR (DMSO-$d_6$, 400 MHz) δ 7.94 (m, 2H), 7.63 (dd, 1H, J=11.29, 1.51 Hz), 7.34 (d, 1H, J=9.54 Hz), 7.14 (m, 3H), 7.05 (m, 1H), 6.83 (s, 1H), 5.58 (t, 2H, J=5.27 Hz), 4.96 (d, 2H, J=4.27 Hz), 4.70 (s, 1H), 3.46 (s, 3H), 1.96 (s, 6H), 1.45 (s, 6H); MS m/e 609.16 (M+H$^+$); HPLC (XBridge 5μ C18 4.6×50 mm, 4 mL/min, Solvent A: 10% MeOH/water with 0.2% $H_3PO_4$, Solvent B: 90% MeOH/water with 0.2% $H_3PO_4$, gradient with 0-100% B over 4 minutes): 2.56 minutes.

Alternatively, Example 9 was prepared as follows:

To a 1 L 3-necked round bottom flask under nitrogen was added methyltetrahydrofuran ("MeTHF", 6.9 kg), 2-(1-(4-bromo-2-fluorophenyl)-2-(2-(2,6-dichlorophenyl)propan-2-yl)-1H-imidazol-4-yl)propan-2-ol (1.994 kg, 4.1 moles) and (2-fluoro-6-(methylsulfonyl)-4-(4,4,5,5-tetramethyl-1,3,2-dioxaborolan-2-yl)phenyl)methanol (1.38 kg, 4.19 moles). The mixture was agitated at 23° C. for 15 min until all the solids dissolved. At the conclusion of this period, (oxydi-2,1-phenylene)bis(diphenylphosphine) (0.022 kg, 0.041 moles) and Pd(OAc)$_2$ (0.01 kg, 0.045 moles) were added as a slurry via a subsurface line. Upon completion of addition, the mixture was rinsed with additional MeTHF (1.65 kg). The resulting mixture was evacuated to less than 80 Torr and backfilled with nitrogen. This process was repeated two more times. After completion of the degassing sequence, the reaction mixture was agitated for at least 15 min and a clear, golden color was observed. In a separate reaction vessel, a solution of potassium hydroxide (0.352 kg) in water (10.00 kg) was prepared and degassed by sparging the solution with nitrogen gas for at least 15 min prior to use. The KOH solution (10.35 kg) was transferred into the reactor by vacuum. The reaction temperature exhibited a known exotherm from 20° C. to 29° C. Upon completion of addition, the resulting biphasic mixture was degassed by a series of pressure swings. The mixture was warmed to between 45-50° C. where it was stirred for at least 2 h. After this time, the reaction mixture was analyzed by HPLC, which indicated the reaction was complete. The reaction mixture was cooled to 23° C. and the stirring was stopped. The mixture was allowed to separate for 30 min and the lower spent KOH stream was removed. The product rich organic was passed through a column of thiourea functionalized silica gel (0.782 kg) (Silicycle) at ~0.1 kg per min to remove the palladium. The product rich organic phase was washed with a 5% NaHCO$_3$ solution (5 vol) and the phases separated. The organic phase was washed with water (5 vol) and the organic and aqueous phases separated.

The product rich organic phase was polish filtered into a clean reaction vessel and then concentrated to ~8 volumes (~16 L) under vacuum (80 Torr, Tjacket=60° C.). Once at the prescribed volume, the reaction mixture was allowed to cool to 25° C. Once at the prescribed temperature the reaction mixture was seeded with 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol (0.5%, 0.008 kg). The resulting slurry was stirred at 25° C. for about 18 h. At the conclusion of this period, the reaction mixture was concentrated to ~8 L under vacuum (150 Torr, Tjacket=60° C.). Once at the prescribed volume, the reaction mixture was heated to 50° C. and isopropyl acetate (IPAc, 13.90 kg) was added to the reactor during a 90 min period. Upon completion of addition, the reaction mixture was cooled to 25° C. during a 3 h period. Once at the prescribed temperature the reaction mixture was stirred at room temperature for about 16 h. At the conclusion of this period, the reaction mixture was filtered, deliquored, and washed with additional IPAc (10.4 kg). The filter cake was dried via suction on the filter under a stream of dry nitrogen to yield a white solid. The white solid was transferred to a dryer and dried at 50° C. under full vacuum to afford 2.03 kg of product (81% yield, 99.40 AP, 98 wt %).

Example 10

2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}$CD$_3$)$_2$]propan-2-ol

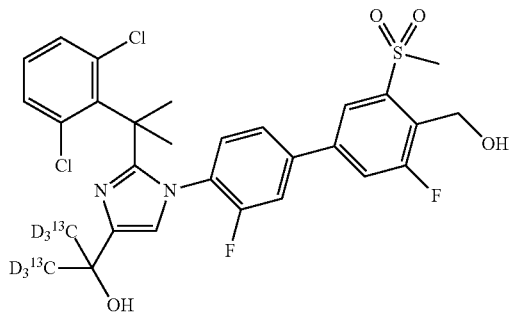

Preparation of 2-(1-(4-bromo-2-fluorophenyl)-2-(2-(2,6-dichlorophenyl)propan-2-yl)-1H-imidazol-4-yl [($^{13}$CD$_3$)$_2$]propan-2-ol

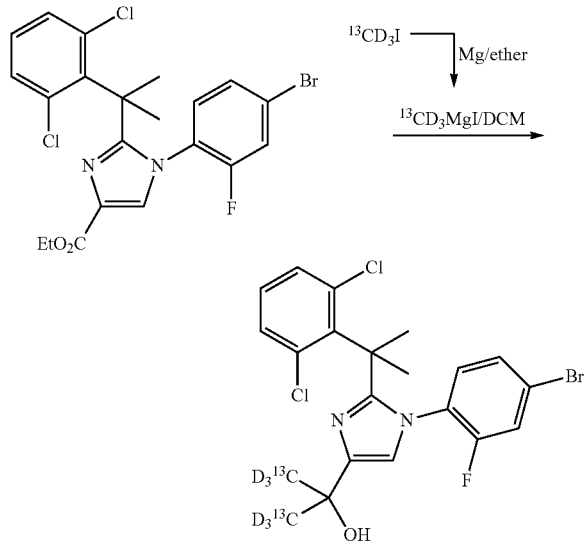

Oven-dried magnesium (86 mg, 3.52 mmol) and anhydrous diethyl ether (3.20 mL) were transferred to an oven-dried 25 mL 14/20 round bottom flask under argon. [$^{13}$CD$_3$]-Iodomethane (467 mg, 3.20 mmol) was added at room temperature and stirred at 33° C. for 1 hour. Visual signs indicated that the Grignard reagent formed (clear suspension changed to cloudy mixture with frothing and exotherm). The solution was cooled to room temperature and transferred via cannula to a chilled solution (ice/water bath) of ethyl 1-(4-bromo-2-fluorophenyl)-2-(2-(2,6-dichlorophenyl)propan-2-yl)-1H-imidazole-4-carboxylate (400 mg, 0.800 mmol) in anhydrous dichloromethane (2.60 mL) under argon. The flask in which the Grignard reagent was prepared was rinsed with anhydrous ether (2×400 μL) and transferred via cannula to the ethyl ester-containing flask. The reaction mixture was allowed to slowly warm to room temperature and stirred for 1 hour. HPLC analysis indicated <0.3% of starting material was present. The reaction was cooled to 0° C., diluted with anhydrous dichloromethane (800 μL) and quenched by the slow, careful addition of sat. aqueous ammonium chloride (8 mL). The two layers were separated, and the aqueous layer was extracted with dichloromethane (3×4 mL). The combined organic extracts were concentrated in vacuo to obtain 443.5 mg of crude product as a white solid. The crude product described above was combined with 244.3 mg (white solid) obtained from a similar reaction. The combined product was purified by silica gel flash chromatography (Isco RediSep cartridge, 12 g) and eluted with 10 to 20% EtOAc in hexane. 30 mL fractions were collected. The fractions were checked by TLC (Silica, 50% EtOAc, 50% hexane, R$_f$=0.41) and HPLC. The pure product-containing fractions were combined and concentrated in vacuo to yield 531.2 mg of product as a white solid (90% yield): $^1$H-NMR (400 MHz, CD$_3$OD) δ ppm: 6.47-7.58 (m, 7H), 2.01 (br s, 6H). HPLC: (YMC ODS-AQ, 3 μm, 150×4.6 mm, Mobile Phase A=0.05% TFA in H$_2$O, Mobile Phase B=0.05% TFA in ACN, 0 min 50% B, 9 min 95% B, 15 min 95% B, 15.5 min 50% B. Flow rate=1 ml/min) T$_r$=9.23 min (at 220 nm, Chemical purity=98.8%), LCMS (+ ion) m/z=487 (0%), 493 (59%), 495 (100%), 497 (47%), 498 (8%).

Preparation of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl) [($^{13}$CD$_3$)$_2$]propan-2-ol

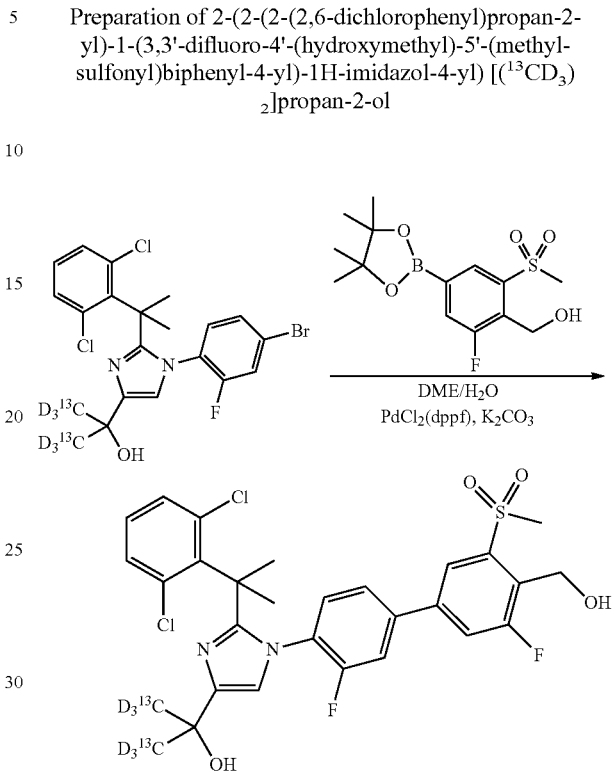

To a 25 mL 14/20 round bottom flask under argon was added 2-(1-(4-bromo-2-fluorophenyl)-2-(2-(2,6-dichlorophenyl)propan-2-yl)-1H-imidazol-4-yl)[($^{13}$CD$_3$)$_2$]propan-2-ol (0.283 g, 0.572 mmol), (2-fluoro-6-(methylsulfonyl)-4-(4,4,5,5-tetramethyl-1,3,2-dioxaborolan-2-yl)phenyl) methanol (0.227 g, 0.686 mmol), 1,1'-Bis (diphenylphosphino)-ferrocene-palladium(II)dichloride dichloromethane complex (0.094 g, 0.114 mmol), potassium carbonate (0.237 g, 1.716 mmol), DME (4.30 ml) and water (0.215 ml) that had been previously sparged with argon. The mixture was heated to 80° C. for 1 hour. HPLC and LCMS analysis indicated starting material had been consumed. The reaction mixture was cooled with an ice-water bath, partitioned between dichloromethane (10 mL) and water (10 mL). The aqueous layer was extracted with dichloromethane (3×10 mL). The combined organic extracts were concentrated in vacuo to give 643.6 mg as a dark semi-solid.

Previously, a similar reaction for the preparation of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}$CD$_3$)$_2$]propan-2-ol had been completed that afforded 462.3 mg of a dark solid. The crude products from both experiments were combined and purified by silica gel flash chromatography (Isco RediSep cartridge, 80 g) after dissolving in dichloromethane and pre-absorbing onto silica gel. The flash column was eluted with 25-50% EtOAc in hexane. 30 mL fractions were collected. Fractions were checked by TLC (Silica, 50% EtOAc, 50% hexane, R$_f$=0.09) and HPLC before combining the pure product-containing fractions and concentrating in vacuo to give 468.3 mg of 2-(2-(2-(2,6-dichlorophenyl)propan-2-yl)-1-(3,3'-difluoro- 4'-(hydroxymethyl)-5'-(methylsulfonyl)biphenyl-4-yl)-1H-imidazol-4-yl)[($^{13}CD_3$)$_2$]propan-2-ol as a yellow solid.

This material was further purified by recrystallization in acetone (4 mL) at 65° C., cooled slowly to 25° C. over 5 hours (crystals started to form at 40° C.) then cooled to 0° C. for an additional 30 minutes. The solid was collected by filtration, rinsed with cold acetone and dried in vacuo to give 66.2 mg of the title compound as an off-white solid.

The mother liquor from this first recrystallization was concentrated and the residue was recrystallized from a minimal amount of acetone (1 mL) using the same procedure as outlined above to obtain a second crop of 276.4 mg of crystalline product as an off-white solid.

The mother liquor from the second recrystallization was concentrated and purified by preparative HPLC, $T_r$=15.0 min (Prep HPLC conditions: Synergi Hydro-RP column, 4μ, 80 Å, 21.2×250 mm, Mobile Phase A=$H_2O$, Mobile Phase B=ACN, 0 min 30% B, 25 min 100% B. Flow rate=16.0 ml/min. UV at 220 nm.)

The 3 purified isolates were combined to give 401.1 mg of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}CD_3$)$_2$]propan-2-ol as a pale yellow solid (64% yield). $^1$H-NMR (400 MHz, DMSO-$d_6$)) δ ppm: 7.86-7.96 (m, 2H), 7.62 (dd, J=11.33 Hz, 2.01 Hz, 1H), 7.33 (dd, J=8.31 Hz, 1.76 Hz, 1H), 7.09-7.19 (m, 3H), 6.99-7.09 (m, 1H), 6.81 (s, 1H), 5.53-5.62 (m, 1H), 4.89-4.99 (m, 2H), 4.67 (t, J=3.15 Hz, 1H), 3.45 (s, 3H), 2.08 (residual acetone, 8 mol %), 1.95 (s, 6H). $^{13}$C-NMR (400 MHz, D6-DMSO) 29.61 (t, J=109.88 Hz)

HPLC: (YMC ODS-AQ, 3 μm, 150×4.6 mm, Mobile Phase A=0.05% TFA in $H_2O$, Mobile Phase B=0.05% TFA in ACN, 0 min 50% B, 9 min 95% B, 15 min 95% B, 15.5 min 50% B. Flow rate=1 ml/min) $T_r$=9.66 min (at 220 nm, Chemical purity=99.8%). LCMS (+ ion) m/z=609 (0%), 617 (100%), 618 (31%), 619 (74%), 620 (22%), 621 (16%), 622 (4.3%), 623 (1.3%).

Examples 11-20

The following compounds were made in a similar manner to that described in Example 1, by substituting various phenyl acetonitrile reagents in place of 2-(phenyl)-2-methylpropanenitriles as the starting material:

| No. | Name | Structure | Data |
| --- | --- | --- | --- |
| 11 | 2-(2-(2,4-dichlorobenzyl)-1-(3,3'-difluoro-4'-(hydroxymethyl)-5'-(methylsulfonyl)biphenyl-4-yl)-1H-imidazol-4-yl)propan-2-ol | 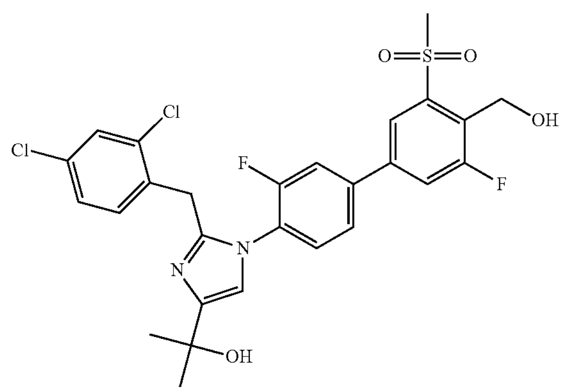 [SMILES: CC(C)(O)c1cn(-c2ccc(-c3cc(F)c(CO)c(S(C)(=O)=O)c3)cc2F)c(Cc2ccc(Cl)cc2Cl)n1] | MS (ES): 581.3, 583.3 [M + H]$^+$ |
| 12 | 2-(1-(3,3'-difluoro-4'-(hydroxymethyl)-5'-(methylsulfonyl)biphenyl-4-yl)-2-(2-(trifluoromethyl)benzyl)-1H-imidazol-4-yl)propan-2-ol | 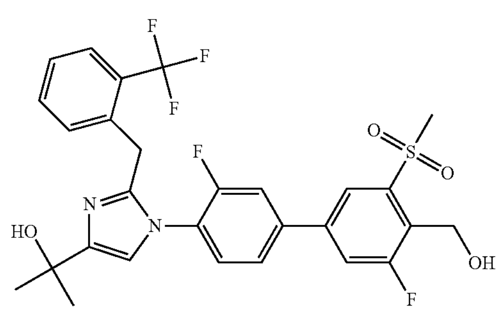 [SMILES: CC(C)(O)c1cn(-c2ccc(-c3cc(F)c(CO)c(S(C)(=O)=O)c3)cc2F)c(Cc2ccccc2C(F)(F)F)n1] | MS (ES): 581.3 [M + H]$^+$ |

-continued

| No. | Name | Structure | Data |
|---|---|---|---|
| 13 | 2-(1-(3-chloro-3'-fluoro-4'-(hydroxymethyl)-5'-(methylsulfonyl)biphenyl-4-yl)-2-(2-chloro-4-fluorobenzyl)-1H-imidazol-4-yl)propan-2-ol | 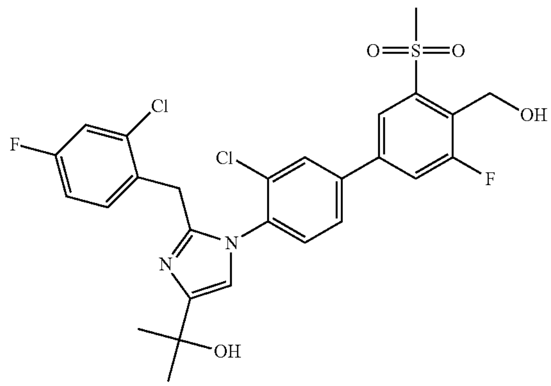 [SMILES: CC(C)(O)c1cn(-c2ccc(-c3cc(F)c(CO)c(S(C)(=O)=O)c3)cc2Cl)c(Cc2ccc(F)cc2Cl)n1] | MS (ES): 581.3, 583.3 [M + H]+ |
| 14 | 2-(2-(2-chloro-4-fluorobenzyl)-1-(3,3'-difluoro-4'-(hydroxymethyl)-5'-(methylsulfonyl)biphenyl-4-yl)-1H-imidazol-4-yl)propan-2-ol | 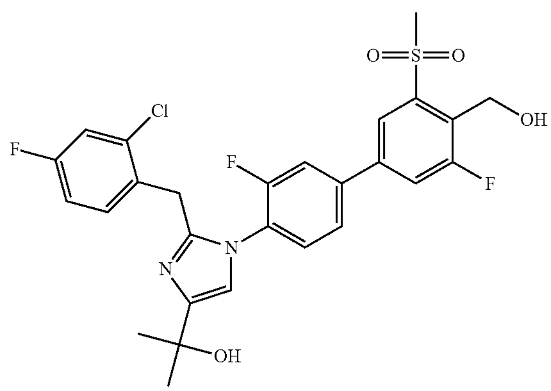 [SMILES: CC(C)(O)c1cn(-c2ccc(-c3cc(F)c(CO)c(S(C)(=O)=O)c3)cc2F)c(Cc2ccc(F)cc2Cl)n1] | MS (ES): 565.3 [M + H]+ |
| 15 | 2-(2-(2,4-dichlorobenzyl)-1-(3'-fluoro-4'-(hydroxymethyl)-5'-(methylsulfonyl)biphenyl-4-yl)-1H-imidazol-4-yl)propan-2-ol | 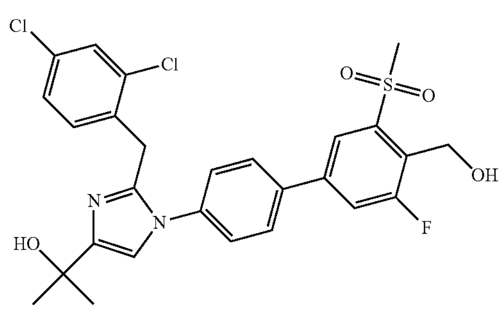 [SMILES: CC(C)(O)c1cn(-c2ccc(-c3cc(F)c(CO)c(S(C)(=O)=O)c3)cc2)c(Cc2ccc(Cl)cc2Cl)n1] | MS (ES): 563.2, 565.2 [M + H]+ |
| 16 | 2-(1-(3,3'-difluoro-4'-(hydroxymethyl)-5'-(methylsulfonyl)biphenyl-4-yl)-2-(2-fluorobenzyl)-1H-imidazol-4-yl)propan-2-ol | 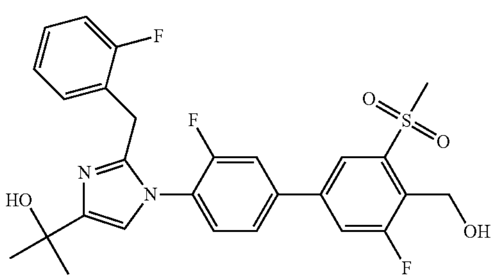 [SMILES: CC(C)(O)c1cn(-c2ccc(-c3cc(F)c(CO)c(S(C)(=O)=O)c3)cc2F)c(Cc2ccccc2F)n1] | MS (ES): 531.2 [M + H]+ |

-continued

| No. | Name | Structure | Data |
|---|---|---|---|
| 17 | 2-(1-(3'-fluoro-4'-(hydroxymethyl)-5'-(methylsulfonyl)biphenyl-4-yl)-2-(2-methylbenzyl)-1H-imidazol-4-yl)propan-2-ol | 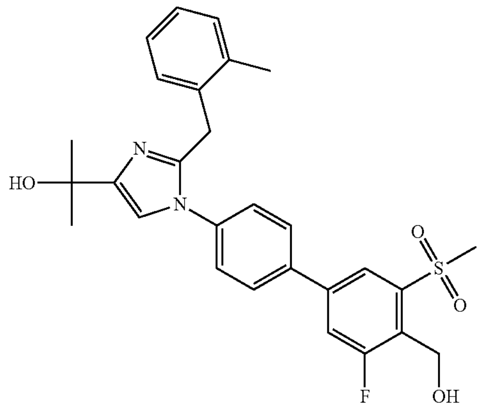 [SMILES: Cc1ccccc1Cc1nc(C(C)(C)O)cn1-c1ccc(-c2cc(F)c(CO)c(S(C)(=O)=O)c2)cc1] | MS (ES): 509.5 [M + H]+; 531.2 [M + Na]+ |
| 18 | 2-(2-(2,6-dichlorobenzyl)-1-(3'-fluoro-4'-(hydroxymethyl)-5'-(methylsulfonyl)biphenyl-4-yl)-1H-imidazol-4-yl)propan-2-ol | 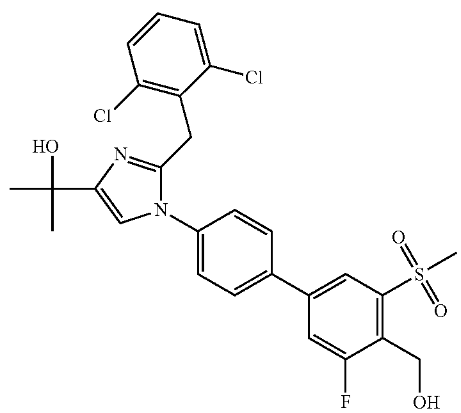 | MS (ES): 586.5 [M + H]+ |
| 19 | 2-[2-(2-Chloro-5-fluoro-benzyl)-1-(3'-fluoro-4'-hydroxymethyl-5'-methanesulfonyl-biphenyl-4-yl)-1H-imidazol-4-yl]-propan-2-ol | 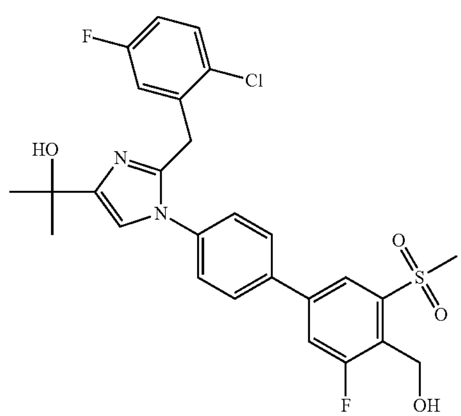 [SMILES: CC(C)(O)c1cn(-c2ccc(-c3cc(F)c(CO)c(S(C)(=O)=O)c3)cc2)c(Cc2cc(F)ccc2Cl)n1] | MS (ES): 547.3 [M + H]+ |

| No. | Name | Structure | Data |
|---|---|---|---|
| 20 | 2-[2-(2-Chloro-benzyl)-1-(3,3'-difluoro-4'-hydroxymethyl-5'-methanesulfonyl-biphenyl-4-yl)-1H-imidazol-4-yl]-propan-2-ol | 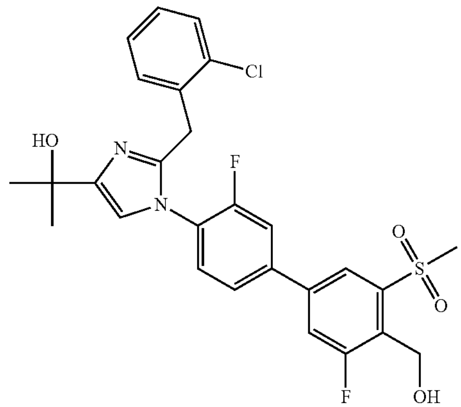 [SMILES: CC(C)(O)c1cn(-c2ccc(-c3cc(F)c(CO)c(S(C)(=O)=O)c3)cc2F)c(Cc2ccccc2Cl)n1] | MS (ES): 547.3 [M + H]+ |

Example 21

Example for Compound 21

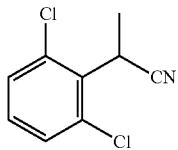

Into a 1 L flask was weighed 25.0 g (134 mmol) of 2,6-dichlorophenylacetonitrile and 250 mL of anhydrous THF. The resulting solution was cooled to −70° C. and 134 mL of 1.0 M potassium tert-butoxide (1.0 M) in THF was added followed by 8.4 mL of iodomethane (1.0 eq). The reaction was stirred at −70° C. for 1 h then was allowed to warm to room temperature over 3 h. The reaction was concentrated in vacuo to remove THF then was washed into a separatory funnel with ethyl acetate and 1 M HCl. The ethyl acetate was separated, washed with bisulfite, brine, was dried ($Na_2SO_4$), and concentrated in vacuo. The residue was purified by silica gel flash chromatography (Biotage, 300 g $SiO_2$, gradient elution from 100% hexanes to 10% ethyl acetate over 1 h). Appropriate fractions were combined and concentrated in vacuo to afford the desired product as a colorless oil, ~99% pure by GC, yield: 12.2 g (45%). $^1$H-NMR (CDCl$_3$, 400 MHz) δ 7.36 (d, J=8 Hz, 2H), 7.22 (t, J=8 Hz, 1H), 4.84 (q, J=7 Hz, 1H), 1.07 (d, J=7 Hz, 3H).

Compound 21 was made in a similar matter to that described in Example 1 using appropriate aniline and 2-(phenyl)propanenitrile as starting material.

| No. | Name | Structure | Data |
|---|---|---|---|
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol | 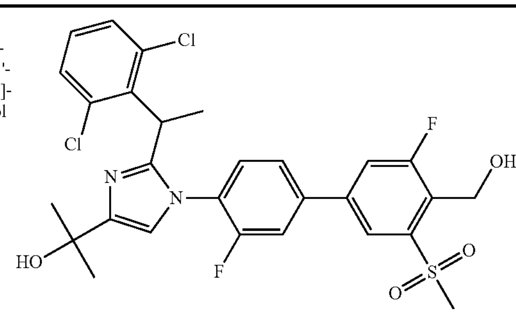 | |

Compound 11 has the following NMR characteristics: 1H NMR (400 MHz, CDCl$_3$) δ 8.10 (d, J=1.2, 1H), 7.59 (dd, J=9.9, 1.8, 1H), 7.47-7.37 (m, 2H), 7.24 (dd, J=5.3, 3.2, 2H), 7.13 (dd, J=8.3, 2.1, 1H), 7.05 (d, J=8.4, 1H), 6.89 (s, 1H), 5.10 (d, J=4.4, 2H), 4.09 (s, 2H), 3.30 (s, 3H), 3.25 (d, J=17.4, 1H), 2.86 (s, 1H), 1.63 (s, 6H).

Compound 12 has the following NMR characteristics: 1H NMR (400 MHz, DMSO) δ 8.06 (d, J=8.7, 2H), 7.99-7.86 (m, 1H), 7.70 (d, J=8.3, 1H), 7.58 (m, 3H), 7.40 (t, J=7.6, 1H), 7.21 (d, J=7.7, 1H), 7.13 (s, 1H), 5.57 (t, J=5.3, 1H), 4.95 (d, J=4.7, 2H), 4.81 (s, 1H), 4.13 (s, 2H), 3.45 (s, 3H), 1.46 (s, 6H).

Compound 13 has the following NMR characteristics: 1H NMR (400 MHz, CDCl$_3$) δ 8.10 (s, 1H), 7.71 (d, J=2.0, 1H), 7.60 (dd, J=9.9, 1.8, 1H), 7.49 (dd, J=8.2, 2.1, 1H), 7.22 (d, J=8.2, 1H), 7.12 (dd, J=8.6, 6.1, 1H), 6.96 (dd, J=8.5, 2.6, 1H), 6.89-6.78 (m, 2H), 5.10 (s, 2H), 4.05 (s, 2H), 3.31 (s, 3H), 3.00 (s, 1H), 2.77 (s, 1H), 1.63 (2, J=5.5, 6H).

Compound 14 has the following NMR characteristics: 1H NMR (400 MHz, DMSO) δ 7.85 (t, J=4.5, 2H), 7.70 (dd, J=11.4, 1.8, 1H), 7.50 (dd, J=8.3, 1.7, 1H), 7.35 (t, J=8.2, 1H), 7.09 (dd, J=8.8, 2.6, 1H), 7.03-6.80 (m, 3H), 5.35 (t, J=5.3, 1H), 4.73 (d, J=4.1, 2H), 4.56 (s, 1H), 3.80 (s, 2H), 3.38 (t, J=6.4, 1H), 3.23 (s, 3H), 1.21 (s, 6H).

Compound 15 has the following NMR characteristics: 1H NMR (400 MHz, CDCl$_3$) δ 8.11 (d, J=1.2, 1H), 7.72-7.53 (m, 3H), 7.28 (dd, J=18.0, 4.9, 5H), 7.15 (dd, J=8.3, 2.1, 1H), 7.05 (d, J=8.4, 1H), 6.96 (s, 1H), 5.09 (s, 2H), 4.12 (s, 2H), 3.30 (s, 3H), 3.28 (s, 1H), 2.93 (s, 1H), 1.64 (s, 6H).

Compound 16 has the following NMR characteristics: 1H NMR (400 MHz, CDCl$_3$) δ 8.09 (s, 1H), 7.60 (dd, J=9.9, 1.8, 1H), 7.39 (m, 2H), 7.23 (t, J=8, 1H), 7.18-7.06 (m, 2H), 7.00 (m, 1H), 6.89-6.81 (m, 2H), 5.10 (dd, J=7.0, 1.6, 2H), 4.06 (s, 2H), 3.30 (s, 3H), 2.92 (t, J=7.0, 1H), 2.70 (s, 1H), 1.64 (s, 6H).

Compound 17 has the following NMR characteristics: 1H NMR (400 MHz, CDCl$_3$) δ 8.10 (s, 1H), 7.64-7.55 (m, 3H), 7.25 (m, 2H), 7.16-7.00 (m, 3H), 6.92 (s, 1H), 6.81 (d, J=7.5, 1H), 5.08 (dd, J=7.1, 1.7, 2H), 4.02 (s, 2H), 3.28 (s, 3H), 2.90 (t, J=7.1, 1H), 2.76 (s, 1H), 2.16 (d, J=8.6, 3H), 1.64 (s, 6H).

Compound 18 has the following NMR characteristics: 1H NMR (400 MHz, CDCl$_3$) δ 8.12 (s, 1H), 7.70-7.59 (m, 3H), 7.45 (d, J=8.4, 2H), 7.24 (d, J=8.0, 2H), 7.16-7.07 (m, 1H), 6.85 (s, 1H), 5.10 (d, J=5.6, 2H), 4.31 (s, 2H), 3.30 (s, 3H), 3.07 (s, 1H), 2.94 (t, J=7.0, 1H), 1.55 (s, 6H).

Compound 19 has the following NMR characteristics: 1H NMR (400 MHz, CDCl$_3$) δ 8.11 (d, J=1.1, 1H), 7.62 (ddd, J=12.0, 8.4, 1.8, 3H), 7.28-7.26 (m, 3H), 6.97 (s, 1H), 6.93-6.76 (m, 2H), 5.09 (s, 2H), 4.14 (s, 2H), 3.29 (br s, 4H), 2.91 (s, 1H), 1.65 (s, 6H).

Compound 20 has the following NMR characteristics: 1H NMR (400 MHz, CDCl$_3$) δ 8.08 (d, J=1.1, 1H), 7.57 (dd, J=9.9, 1.8, 1H), 7.38 (ddd, J=10.3, 9.2, 2.0, 2H), 7.23-7.17 (m, 2H), 7.18-7.01 (m, 3H), 6.89 (d, J=0.7, 1H), 5.09 (s, 2H), 4.14 (s, 2H), 3.37 (s, 1H), 3.30 (s, 3H), 2.92 (s, 1H), 1.64 (s, 6H).

Compound 21 has the following NMR characteristics: 1H NMR (400 MHz, CDCl$_3$) δ 7.97 (s, 1H), 7.47 (dd, J=9.8, 1.6, 1H), 7.18 (d, J=10.6, 1H), 7.12-7.04 (m, 2H), 6.96 (d, J=7.9, 2H), 6.90-6.81 (m, 1H), 6.79 (s, 1H), 5.13 (s, 2H), 4.94 (q, J=7.0, 1H), 3.82 (s, 1H), 3.39 (d, J=24.5, 1H), 3.36 (s, 3H), 1.81 (d, J=7.1, 3H), 1.63 (s, 6H).

Standard physiological, pharmacological and biochemical procedures are available for testing the compounds to identify those that possess biological activities that modulate the activity of the LXRs (LXR$_\alpha$ and LXR$_\beta$). Such assays include, for example, biochemical assays such as binding assays, fluorescence polarization assays, FRET-based coactivator recruitment assays (see, generally, Glickman et al., J. Biomolecular Screening (2002), Vol. 7, No. 1, pp. 3-10), as well as cell based assays including the co-transfection assay, the use of LBD-Gal 4 chimeras and protein-protein interaction assays, (see, Lehmann. et al., J. Biol Chem. (1997), Vol. 272, No. 6, pp. 3137-3140).

Compounds of the present invention show unexpected advantages over compounds previously disclosed in the art, such as those disclosed in PCT Publ. No. WO 2007/002563. The present compounds have been shown in an assay(s), such as those described below, to have a desirable partial LXR agonist character with increased potency in human whole blood and low LXRα efficacy. Additionally, the compounds of the present invention also exhibit metabolic stability in a human liver microsomal assay. Such compounds should be more useful in the treatment, inhibition or amelioration of one or more diseases or disorders that are discussed herein.

Example A

Scintillation Proximity Assay (SPA)

The SPA assay measures the radioactive signal generated by the binding of $^3$H-24,25-epoxycholesterol to LXR$_\alpha$-RXR$_\alpha$ or LXR$_\beta$-RXR$_\alpha$ heterodimers The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

Required Materials:
1. Label: $^3$H-24,25-epoxy-cholesterol (NEN Life Science Products/Perkin Elemer))
2. LXR$_\alpha$ lysate: *Baculovirus* expressed LXR$_\alpha$/RXR heterodimer both with a 6-HIS tag produced as a crude lysate
3. LXR$_\beta$ lysate: *Baculovirus* expressed LXR$_\beta$/RXR heterodimer both with a 6-HIS tag produced as a crude lysate
4. SPA beads: Ysi copper His-tag SPA beads (Amersham)
5. Plates: Non-binding surface 384-well plate (Corning)
6. Protein lysate dilution buffer: (20 mM Tris-HCl pH 7.9, 500 mM NaCl, 5 mM Imidazole).
7. 2× SPA Buffer: (40 mM K$_2$HPO$_4$/KH$_2$PO$_4$ pH7.3, 100 mM NaCl, 0.05% Tween 20, 20% Glycerol, 4 mM EDTA)
8. 2× SPA Buffer w/o EDTA: (40 mM K$_2$HPO$_4$/KH$_2$PO$_4$ pH7.3, 100 mM NaCl, 0.05% Tween 20, 20% Glycerol)

Stock Solutions
0.5 M K$_2$HPO$_4$/KH$_2$PO$_4$ pH 7.3
0.5 M EDTA pH 8.0
5 M NaCl
10% Tween-20
Glycerol Preparation of Protein Lysates

*Baculovirus* expression plasmids for human RXR$_\alpha$ (accession No NM_002957), LXR$_\alpha$ (accession No U22662), and LXR$_\beta$ (accession No U07132) were made by cloning the appropriate full-length cDNAs into the pBacPakhis2 vector (Clontech, Calif.) following standard procedures. Insertion of the cDNAs into the pBAcPakhis2 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately 1.25×10$^6$/ml at 27° C., in a total volume of 500 mL per 1 L sized spinner flasks, cultured under standard conditions. To prepare the LXR$_\alpha$ lysate, insect cells were co-transfected with the LXR$_\alpha$ expression cassette at an M.O.I. of 2.0 and with the RXR expression cassette at a M.O.I. of approximately 1.0. To prepare the LXR$_\beta$ lysate, insect cells were co-transfected with the LXR$_\beta$ expression cassette at an M.O.I of approximately 2.0 and with the RXR expression cassette at a M.O.I. of approximately 1.0. In both cases cells were incubated for 48 hours at 27° C. with constant shaking prior to harvesting.

After incubation, cells were harvested by centrifugation and pelleted. Cell pellets were resuspended in two volumes of ice-cold freshly prepared extraction buffer (20 mM Tris pH 8.0, 10 mM Imidazole, 400 mM NaCl, containing one EDTA free protease inhibitor tablet (Roche Catalog No: 1836170) per 10 ml of extraction buffer).

Cells were homogenized slowly on ice using a Dounce homogenizer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) and adjusted for protein concentration and expression level prior to use in screening assays.

Preparation of Screening Reagents

[$^3$H] 24,25 Epoxycholesterol (EC) solution: For a single 384-well plate (or 400 wells), 21 μL of [$^3$H] EC (specific activity 76.5 Ci/mmol, concentration 3.2 mCi/mL) was added to 4.4 mL of 2× SPA buffer to provide for a final concentration of 200 nM. For each additional 384-well plate, an additional 19.1 μL of [$^3$H] EC was added to 4.0 mL of additional 2× SPA buffer. The final concentration of [$^3$H] EC in the well was 50 nM.

$LXR_\alpha$ lysate (prepared as above) was diluted with protein lysate dilution buffer. 1400 μL of diluted $LXR_\alpha$ lysate was prepared per 384-well plate, (or 200 wells) and 1120 μL of diluted $LXR_\alpha$ lysate was prepared for each additional 384-well plate.

$LXR_\beta$ lysate (prepared as above) was diluted with protein lysate dilution buffer. 1400 μL of diluted $LXR_\beta$ lysate was prepared per 384-well plate, (or 200 wells) and 1120 μL of diluted LXRβ lysate was prepared for each additional 384-well plate.

SPA bead solution: For a 384-well plate (or 400 wells), 3.75 mL of 2× SPA buffer w/o EDTA, 2.25 mL of $H_2O$, and 1.5 mL of Ysi His-tag SPA beads (vortex well before taking) were mixed together. For each additional 384-well plate, an additional 3.5 mL of 2× SPA buffer w/o EDTA, 2.1 mL of $H_2O$, and 1.4 mL of Ysi His-tag SPA beads were mixed together.

Procedure:

Appropriate dilutions of each compound were prepared in a 96-well plate and pipetted into the appropriate wells of a 384 well plate at 3.5 μl per well.

9.1 μL of [$^3$H] EC was added to each well of column 2-23 of the multiwell plate.

5 μl of diluted $LXR_\alpha$ lysate was added to each well of column 2-23 on odd rows of the multiwell plate.

5 μL of diluted $LXR_\beta$ lysate was added to each well of column 2-23 on even rows of the multiwell plate.

17.5 μL of SPA bead solution was added to each well of column 2-23 of the multiwell plate.

The plates were covered with clear sealer and placed in an incubator at ambient temperature for approximately 30 minutes.

After incubation plates were analyzed using a luminescent plate reader (MicroBeta, Wallac) using the program n ABASE 3H_384DPM. The setting for n ABASE 3H_384DPM was:

Counting Mode: DPM;
Sample Type: SPA;
ParaLux Mode: low background;
Count time: 30 sec.

Assays for $LXR_\alpha$ and $LXR_\beta$ were performed in the identical manner. The determined Ki represents the average of at least two independent dose response experiments. The binding affinity for each compound may be determined by non-linear regression analysis using the one site competition formula to determine the $IC_{50}$ where:

$$Y=\text{Bottom}+(\text{Top}-\text{Bottom})/(1+10^{X-\log IC50}).$$

The Ki is than calculated using the Cheng and Prusoff equation where:

$$Ki=IC_{50}/(1+[\text{Concentration of Ligand}]/Kd \text{ of Ligand}).$$

For this assay, typically the Concentration of Ligand=50 nM and the Kd of EC for the receptor is 200 nM as determined by saturation binding.

The compounds of the invention demonstrated the ability to bind to $LXR_\alpha$ and/or $LXR_\beta$, when tested in this assay.

Example B

Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay, expression plasmids for LXRα and LXRβ are introduced separately via transient transfection into mammalian cells along with a luciferase reporter plasmid that contains one copy of a DNA sequence that is bound by LXR-RXR heterodimers (LXRE; Willy, P. et. al. 1995). LXRs heterodimerize with the endogenous RXR. Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials

CV-1 African Green Monkey Kidney Cells

Co-transfection expression plasmids, comprising full-length $LXR_\alpha$ (pCMX-h $LXR_\alpha$ or $LXR_\beta$ (pCMX-h$LXR_\beta$), reporter plasmid (LXREx1-Tk-Luciferase), and control (pCMX-Galactosidase expression vector) (Willey et al. Genes & Development 9 1033-1045 (1995)).

Transfection reagent such as FuGENE6 (Roche).

1× cell lysis buffer:
22.4 mM Tricine pH 8.0
0.56 mM EGTA pH 8.0
5.6 mM $MgSO_4$
0.6% Triton X-100
5.6% glycerol 10× luciferase substrate solution:
10 mM HEPES pH 6.5
2.75 mM D-Luciferin
0.75 mM Coenzyme-A
3.7 mM ATP
96 mM DTT Preparation of Screening Reagents CV-1 cells were prepared 24 hours prior to the experiment by plating them into T-175 flasks or 500 $cm^2$ dishes in order to achieve 70-80% confluency on the day of the transfection. The number of cells to be transfected was determined by the number of plates to be screened. Each well of a 384 well plate requires ~8000 cells. DNA Transfection Reagent was prepared by mixing the required plasmid DNAs with a cationic lipid transfection reagent FuGENE6 (Roche) by following the instructions provided with the reagents. Optimal DNA amounts were determined empirically per cell line and size of vessel to be transfected. For each T175 cm$^2$ flask a total of 20 μg of DNA, 60 μl of Fugene 6 and 1 ml of Optimem was mixed and added. Cells were then incubated at least 5 hours at 37° C. to prepare screening cells.

Luciferase assay reagent was prepared by combining before use:
1 part of 10× Luciferase substrate solution
9 parts of 1× cell lysis buffer.

Procedure

Assay plates were prepared by dispensing 5 μL, of compound per well of a 384 well plate to achieve final compound concentration of 10 μM and no more than 0.5% DMSO. Media was removed from the screening cells, the cells trypsinized, harvested cells by centrifugation, counted, and plated at a density of approximately 8000 cells per well in the 384 well assay plate prepared above in a volume of about 45 μL. Assay plates containing both compounds and screening cells (50 μL, in total volume) were incubated for 20 hours at 37° C.

After incubation with compounds, media was removed from the cells and luciferase assay reagent (30 μL/well) added. After ~2 minutes at ambient temperature, the assay plates were read on a luminometer (PE Biosystems Northstar reader with on-board injectors, or equivalent).

The LXR/LXRE co-transfection assay can be used to establish the $EC_{50}/IC_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethylpropionamide)) or a low control (DMSO/vehicle). The dose response curves are generated from a 10 point curve with concentrations differing by ½ LOG units. Each point represents the average of 4 wells of data from a 384 well plate.

The data from this assay is fitted to the following equation, from which the $EC_{50}$ value may be solved:

$$Y=\text{Bottom}+(\text{Top}-\text{Bottom})/(1+10^{((logEC50-X)*HillSlope)}).$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 2 and normally 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethylpropionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example, 100% inhibition would indicate that the activity of a specific concentration of LXR agonist has been reduced to baseline levels, defined as the activity of the assay in the presence of DMSO only.

Compounds of the present invention were tested in the LXRα assay described immediately above and were shown to have efficacy of less than or equal to 25% of the control compound.

Compounds of the present invention were tested in the LXRβ assay described immediately above and were shown to have efficacy of greater than or equal to 30% of the control compound.

Example C

Human Whole Blood Assay

Human whole blood was collected in EDTA containing tubes and 0.5 mL aliquots were immediately mixed in a 96 well block with the appropriate serial dilution of test compound, in 0.5% DMSO. Compounds were incubated with blood at 37° C. with constant rocking for 4 hours. After incubation, cells were lysed in ABI Nucleic Acid Purification Lysis Solution (Applied Biosystems catalog #4305895) and frozen at −80° C. Following cell lysis, total RNA was purified using an ABI 6100 RNA prep station according to the protocol provided by the manufacturer. cDNAs were synthesized, and mRNAs were quantitated using SYBR-Green Quantitative PCR (Q-PCR) on an ABI Prism 7900HT Sequence Detection System and reagents from Quanta Bioscience Inc (Quanta Bioscience catalog #95047 and 95055).

TABLE 2.1

Primers Used for mRNA Quantitation by RT-PCR

| Gene | Forward Primer | Reverse Primer |
| --- | --- | --- |
| ABCA1 | GGTGATGTTTCTGACCAATGTGA | TGTCCTCATACCAGTTGAGAGAC |
| ABCG1 | GACTGCGTGTCCTGCAAAATC | GATGGGGGCATGATGACAATG |
| L-30 | GCTGGAGTCGATCAACTCTAGG | CCAATTTCGCTTTGCCTTGTC |
| B2M | GGCTATCCAGCGTACTCCAAA | CGGCAGGCATACTCATCTTTT |

The quantity of each mRNA was determined by the ΔΔCT method (Michael W. Pfaffl. A new mathematical model for relative quantification in real-time RT-PCR. Nucleic Acids Research, 2001, Vol. 29, No. 9 e45) and normalized to the quantity of two control mRNAs, i.e. ribosomal protein L-30 (L-30) and beta-2-microglobulin (B2M). The induction of ABCA1 and ABCG1 by test compound was graphed as a percent of the reference compound, 2-(4-(5-(5-cyano-1-(2,4-difluorobenzyl)-6-oxo-4-(trifluoromethyl)-1,6-dihydropyridin-2-yl)thiophen-2-yl)-3-methylphenyl)acetic acid, and potency ($EC_{50}$) and activity (% MAX) were calculated by fitting a sigmoidal response curve as a function of log transformed compound concentration using XLFit software according to the equation y=A+((B−A)/(1+((C/x)^D))). The full LXRα and LXRβ pan agonist 2-(4-(5-(5-cyano-1-(2,4-difluorobenzyl)-6-oxo-4-(trifluoromethyl)-1,6-dihydropyridin-2-yl)thiophen-2-yl)-3-methylphenyl)acetic acid, ($EC_{50}$ 1-2 μM) was used as a reference compound and its maximal activity was defined as 100%.

Compounds of the present invention were tested in the assay described immediately above and were shown to have a potency generally less than 1,000 nM, preferably, less than 100 nM, more preferably less than 20 nM.

Example D

High Throughput (HT) Metabolic Stability in Human Microsomes

The metabolic stability assay evaluates CYP-mediated metabolic stability in vitro using Human liver microsomes after a ten-minute incubation.

Test compound is received as a 3.5 mM stock solution in 100 percent DMSO. Compound is diluted to create a 50 µM acetonitrile (ACN) solution containing 1.4% DMSO, which is then used as a 100× stock for incubation with human liver microsomes. Each compound is tested in duplicate. Compound, NADPH and liver microsome solutions are combined for incubation in three steps:

1) 152 µl of liver microsome suspension, protein concentration of 1.1 mg/ml in 100 mM $NaP_i$, pH 7.4, 5 mM $MgCl_2$ buffer, is pre-warmed at 37° C.
2) 1.7 µl of 50 µM compound (98.6% ACN, 1.4% DMSO) is added to the same tube and pre-incubated at 37° C. for 5 minutes.
3) The reaction is initiated by the addition of 17 µl of pre-warmed 10 mM NADPH solution in 100 mM $NaP_i$, pH 7.4.

Reaction components are mixed well, and 75 µl are immediately transferred into 150 µl quench/stop solution (zero-time point, $T_0$). Reactions are incubated at 37° C. for 10 minutes and then an additional 75 µl aliquot is transferred into 150 µl quench solution. Acetonitrile containing 100 µM DMN (a UV standard for injection quality control), is used as the quench solution to terminate metabolic reactions.

Quenched mixtures are centrifuged at 1500 rpm (~500× g) in an Allegra X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, is then transferred to a separate 96-well plate for UV-LC/MS-MS analysis to determine the per cent of parent compound that is remaining in the mixture.

UV-LC/MS-MS Sample Analysis—Structural Integrity Pre-Analysis

The Metabolic Stability structural integrity pre-analysis is used to assess the purity of compounds being assayed. Compounds are received in 96-well plates as 57 µl of a 3.5 mM DMSO solution. The 3.5 mM compound DMSO stock solutions are diluted 18-fold with a solution containing equal volumes of acetonitrile, isopropanol, and MilliQ-$H_2O$. The resulting solutions (200 µM) are analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflect purity by UV absorbance at 220 nm. Only results for those compounds with purity greater than 50% are reported.

| Metabolic Stability - Structural Integrity HPLC Gradient* | | |
|---|---|---|
| Gradient Time (min) | A % | B % |
| 0.00 | 100 | 0 |
| 4.00 | 0 | 100 |
| 5.00 | 0 | 100 |
| 5.10 | 100 | 0 |
| 6.00 | 100 | 0 |

*Mobile Phase for structural integrity pre-analysis: (A) 98% water, 2% acetonitrile with 10 mM ammonium acetate; (B) 10% water, 90% acetonitrile with 10 mM ammonium acetate Sample Analysis—Incubated Samples MS/MS condition optimization is conducted on a Thermo TSQ Quantum triple-quadropole mass spectrometer equipped with a Heated-electrospray (H-ESI) source by automated infusion to obtain the SRM transitions and their corresponding collision energy values. Compound solutions at a concentration of 20 µM in 1:1 methanol:water are infused at a flow rate of 90 µL/min, then combined with the mobile phase at a flow rate of 50 µL/min before being introduced into the source. All compounds are optimized first using mobile phase A and B (50% A and 50% B), and if necessary, using mobile phase C and D (also with a 50:50 composition). The optimized parameters, including polarity, SRM transition and collision energy, are stored in a Microsoft Access database.

The mass spectrometric conditions obtained from automated infusion are used to analyze incubation samples from the Metabolic Stability assay. The injection volume is 5 µl and the flow rate is 0.8 ml/min. The gradient used is show in the table below. All samples are injected with the gradient using mobile phase A and B first. If necessary (for instance, for chromatographic reasons), samples are re-injected with the same gradient, but using mobile phase C and D. All LC-MS/MS analysis parameters are captured electronically in the raw data files.

| Metabolic Stability - Sample Analysis Gradient* | | |
|---|---|---|
| Gradient Time (min) | A % (or C %) | B % (or D %) |
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

*Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile Peak integration is performed with the Xcalibur™ software. The percent remaining calculation is performed by comparing the LC-MS/MS peak areas from the $T_{10 minute}$ samples to those from the $T_{0 minute}$ samples for each compound.

Compounds of the present invention were tested in the assay described immediately above and were shown to have greater than 80% of parent compound remaining at 10 minutes.

The following Table 1 presents the results of the LXR/LXRE co-transfection assay that measures LXRα EC50 and efficacy, the human whole blood assay (hWBA) that measures the ability of the compounds to bind to LXR and induce ABCA1 gene expression relative to a reference compound, and the microsome metabolic stability assay. $EC_{50}$ values are given in ranges where A is ≤100 nM, B is 101 nM to <1,000 nM and C is >1,000 nM.

TABLE 1
| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 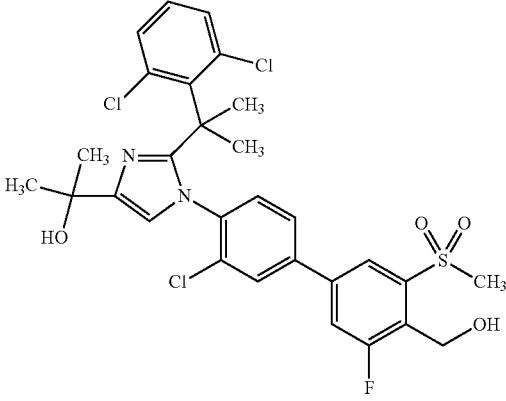 [SMILES: CC(C)(O)c1cn(-c2ccc(-c3cc(F)c(CO)c(S(C)(=O)=O)c3)cc2Cl)c(C(C)(C)c2c(Cl)cccc2Cl)n1] | 3 | A | 6 | A | 16 | >80% |
| 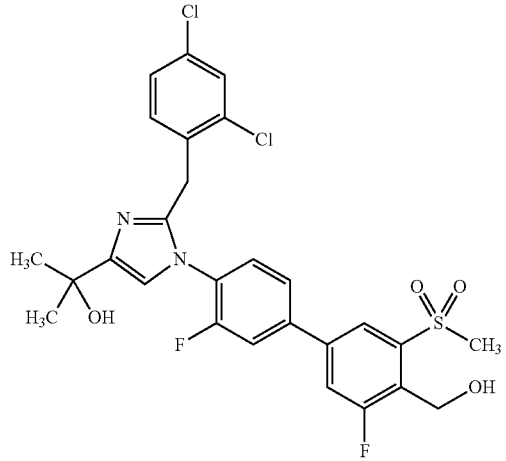 [SMILES: CC(C)(O)c1cn(-c2ccc(-c3cc(F)c(CO)c(S(C)(=O)=O)c3)cc2F)c(Cc2ccc(Cl)cc2Cl)n1] | 11 | C | — | A | 16 | >80% |
| 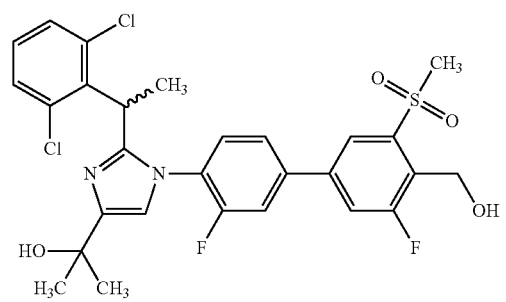 [SMILES: CC(c1c(Cl)cccc1Cl)c1nc(C(C)(C)O)cn1-c1ccc(-c2cc(F)c(CO)c(S(C)(=O)=O)c2)cc1F] | 21 | A | 18 | A | 17 | >80% |

TABLE 1-continued
| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 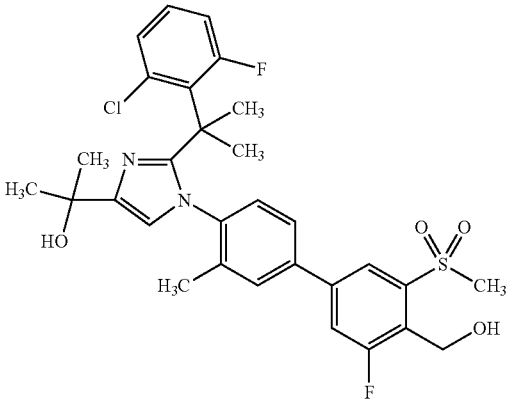 [SMILES: Cc1cc(-c2cc(F)c(CO)c(S(C)(=O)=O)c2)ccc1-n1cc(C(C)(C)O)nc1C(C)(C)c1c(F)cccc1Cl] | 2 | A | 10 | A | 18 | >80% |
| 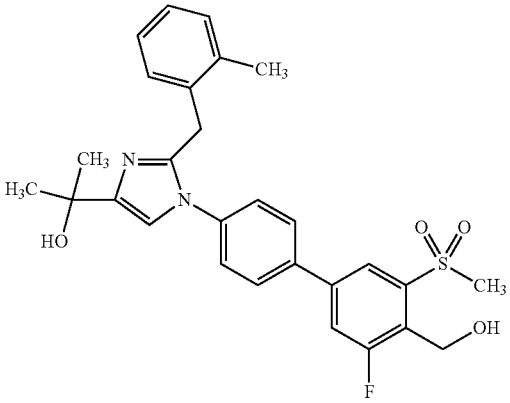 [SMILES: Cc1ccccc1Cc1nc(C(C)(C)O)cn1-c1ccc(-c2cc(F)c(CO)c(S(C)(=O)=O)c2)cc1] | 17 | B | 13 | A | 20 | >80% |
| 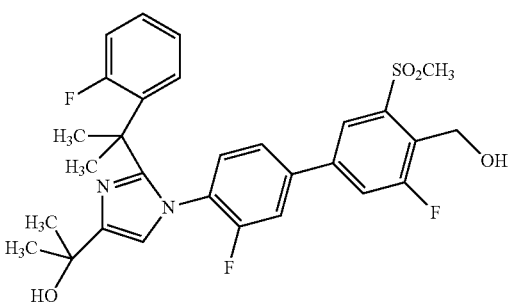 [SMILES: CC(C)(O)c1cn(-c2ccc(-c3cc(F)c(CO)c(S(C)(=O)=O)c3)cc2F)c(C(C)(C)c2ccccc2F)n1] | 8 | A | 10 | A | 23 | >80% |

TABLE 1-continued
| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 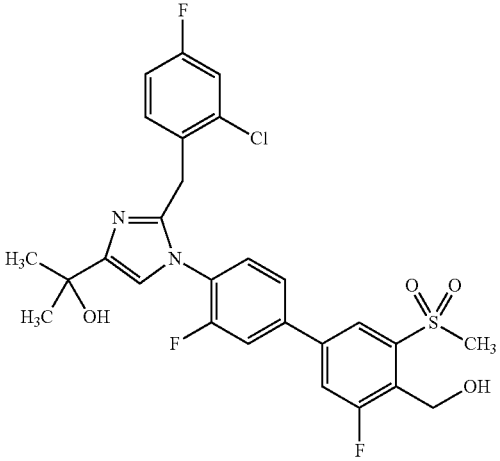 [SMILES: CC(C)(O)c1cn(-c2ccc(-c3cc(F)c(CO)c(S(C)(=O)=O)c3)cc2F)c(Cc2ccc(F)cc2Cl)n1] | 14 | A | 15 | A | 24 | >80% |
| 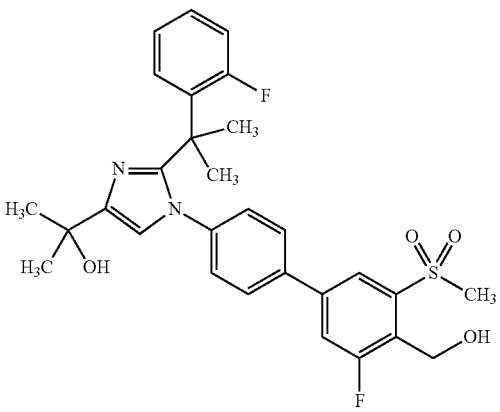 [SMILES: CC(C)(O)c1cn(-c2ccc(-c3cc(F)c(CO)c(S(C)(=O)=O)c3)cc2)c(C(C)(C)c2ccccc2F)n1] | 1 | B | 13 | A | 28 | >80% |
| 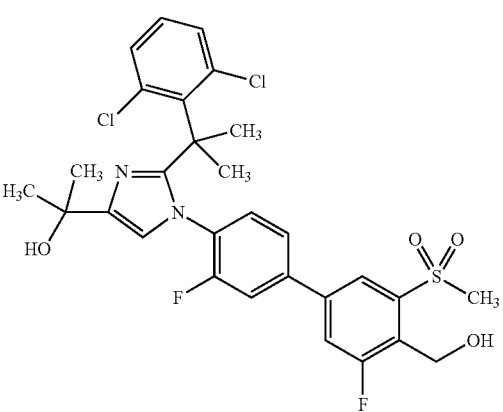 [SMILES: CC(C)(O)c1cn(-c2ccc(-c3cc(F)c(CO)c(S(C)(=O)=O)c3)cc2F)c(C(C)(C)c2c(Cl)cccc2Cl)n1] | 9 | A | 20 | A | 28 | >80% |

TABLE 1-continued

| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 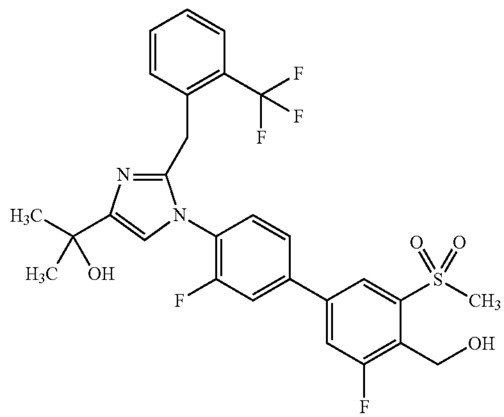 [SMILES: CC(C)(O)c1cn(-c2ccc(-c3cc(F)c(CO)c(S(C)(=O)=O)c3)cc2F)c(Cc2ccccc2C(F)(F)F)n1] | 12 | A | 13 | A | 32 | >80% |
| 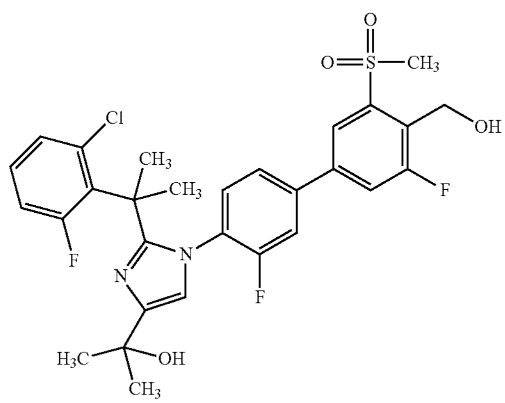 [SMILES: CC(C)(O)c1cn(-c2ccc(-c3cc(F)c(CO)c(S(C)(=O)=O)c3)cc2F)c(C(C)(C)c2c(F)cccc2Cl)n1] | 7 | A | 15 | A | 33 | >80% |
| 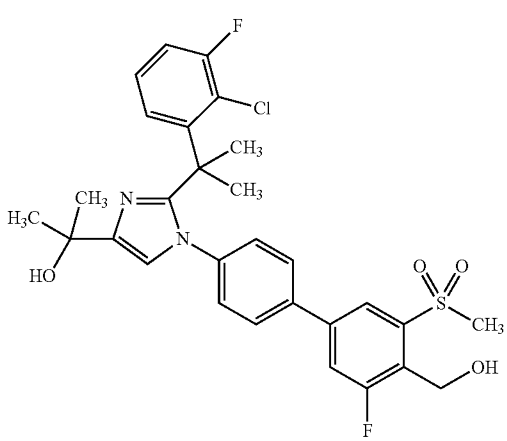 [SMILES: CC(C)(O)c1cn(-c2ccc(-c3cc(F)c(CO)c(S(C)(=O)=O)c3)cc2)c(C(C)(C)c2cccc(F)c2Cl)n1] | 4 | A | 12 | A | 34 | >80% |
| 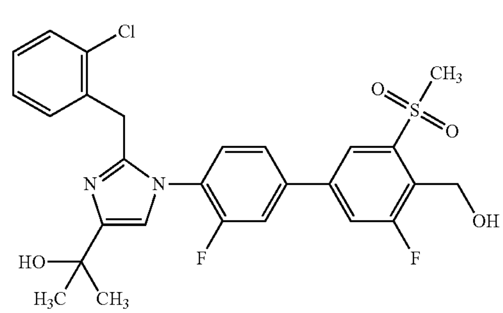 [SMILES: CC(C)(O)c1cn(-c2ccc(-c3cc(F)c(CO)c(S(C)(=O)=O)c3)cc2F)c(Cc2ccccc2Cl)n1] | 20 | B | 15 | A | 35 | >80% |

TABLE 1-continued

| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 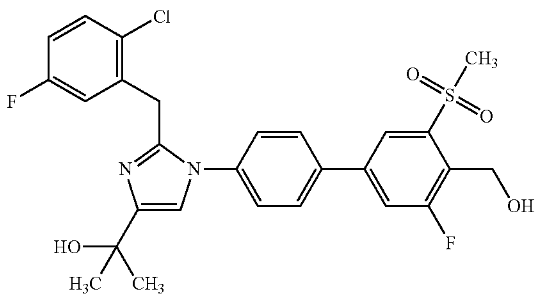 [SMILES: CC(C)(O)c1cn(-c2ccc(-c3cc(F)c(CO)c(S(C)(=O)=O)c3)cc2)c(Cc2cc(F)ccc2Cl)n1] | 19 | C | — | A | 35 | >80% |
| 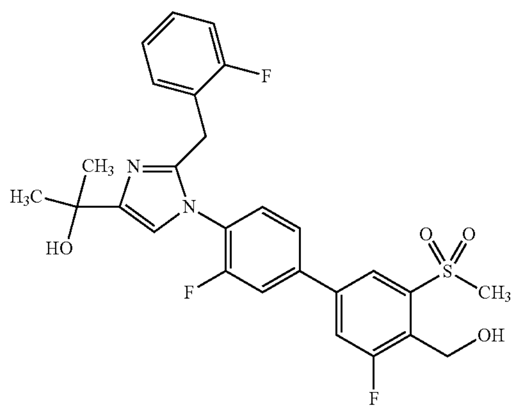 [SMILES: CC(C)(O)c1cn(-c2ccc(-c3cc(F)c(CO)c(S(C)(=O)=O)c3)cc2F)c(Cc2ccccc2F)n1] | 16 | A | 19 | A | 41 | >80% |
| 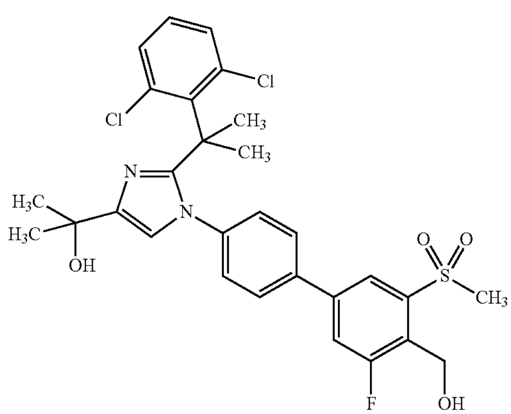 [SMILES: CC(C)(O)c1cn(-c2ccc(-c3cc(F)c(CO)c(S(C)(=O)=O)c3)cc2)c(C(C)(C)c2c(Cl)cccc2Cl)n1] | 5 | A | 25 | A | 43 | >80% |
| 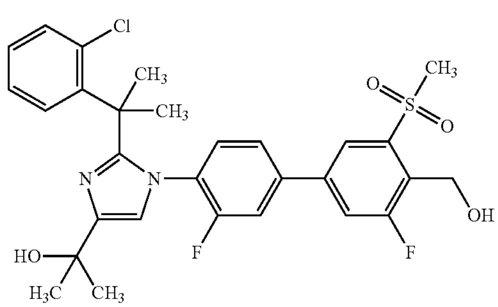 [SMILES: CC(C)(O)c1cn(-c2ccc(-c3cc(F)c(CO)c(S(C)(=O)=O)c3)cc2F)c(C(C)(C)c2ccccc2Cl)n1] | 6 | A | 25 | A | 35 | >80% |

TABLE 1-continued

| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 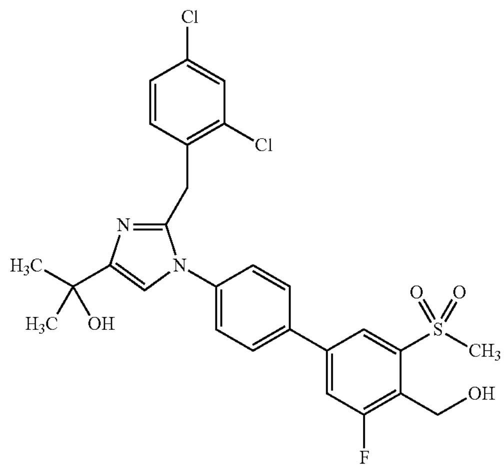 [SMILES: CC(C)(O)c1cn(-c2ccc(-c3cc(F)c(CO)c(S(C)(=O)=O)c3)cc2)c(Cc2ccc(Cl)cc2Cl)n1] | 15 | A | 8 | A | 47 | >80% |
| 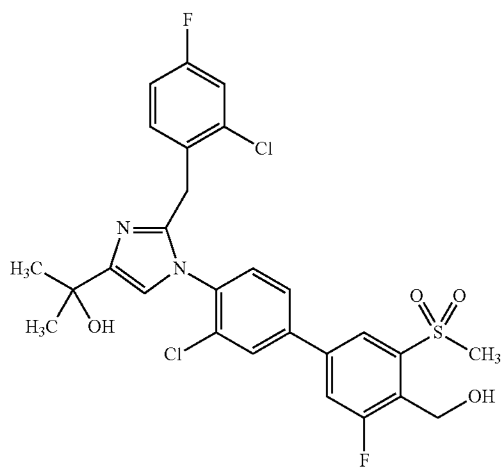 [SMILES: CC(C)(O)c1cn(-c2ccc(-c3cc(F)c(CO)c(S(C)(=O)=O)c3)cc2Cl)c(Cc2ccc(F)cc2Cl)n1] | 13 | A | 18 | A | 50 | >80% |
| 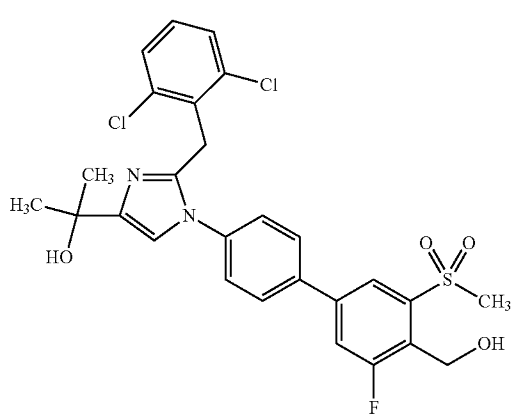 [SMILES: CC(C)(O)c1cn(-c2ccc(-c3cc(F)c(CO)c(S(C)(=O)=O)c3)cc2)c(Cc2c(Cl)cccc2Cl)n1] | 18 | A | 17 | A | 51 | >80% |

TABLE 1-continued

| Structure | # | LxRα EC50 (nM) | LXRα Eff (%) | hWBA hABCA1 L30 EC50 (nM) | hWBA hABCA1 L30 Max P (%) | Human Microsome % Remaining |
|---|---|---|---|---|---|---|
| 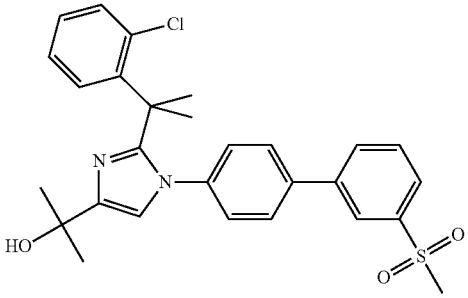 [SMILES: CC(C)(O)c1cn(-c2ccc(-c3cccc(S(C)(=O)=O)c3)cc2)c(C(C)(C)c2ccccc2Cl)n1] | Compound No. 19, Table 1, WO 2007/002563 | B | 38 | C | 55 | >80% |

The above representative data illustrates the unexpected desirable partial LXR agonist character, increased potency in human whole blood, low LXRα efficacy and metabolic stability in a human liver microsomal assay of the compounds of the present invention in comparison to compounds previously disclosed in the art, such as those disclosed in PCT Publ. No. WO 2007/002563.

Example E

In Vivo Potency and Maximum ABCG1 Induction in Cynomolgus Monkey

Compounds of the present invention were tested for their ability to induce the mRNA for the LXR target gene ABCG1 in blood cells when administered orally to cynomolgus monkeys.

Test compounds were formulated in 0.5% carboxymethyl cellulose (CMC, Sigma) and 2% Tween 80 (Sigma) by trituration. Each treatment group contained three male monkeys, each weighing 3.0-6.0 kg at the start of the study. Test compounds were formulated fresh each morning in vehicle, and animals that had been fasted the previous night were dosed between 7 and 7:30 AM by po gavage. For baseline blood cell mRNA determinations, 1 ml of venous blood was collected in an EDTA dry-coated tube and 1 volume of Dulbecco's Phosphate Buffered Saline without calcium or magnesium and 2 volumes of Nucleic Acid Purification Lysis Solution (Applied Biosystems, Inc.) were added. Samples were frozen at −80° C. prior to RNA isolation and analysis. Test compounds were dosed following the baseline sample collection. At 5 hr post-dose, venous blood was collected and processed as above for RNA determinations. An additional 0.5 ml of blood was also collected and analyzed for compound plasma concentrations.

RNA Isolation.

Frozen samples were allowed to thaw at room temperature, and then placed on ice. Total RNA was isolated on the ABI 6100 using a pre-loaded protocol according to the manufacturer's instructions (ABI Manual #4332809 Rev. B).

cDNA Synthesis and Q-PCR Reactions.

qScript cDNA Synthesis Kit from Quanta Biosciences, Inc. was used to generate first-strand cDNA from each total RNA sample. 20 µl Reactions were carried out in 96-well Eppendorf AG twin-tec PCR plates on a MJ Research, Inc. model PTC-200 DNA Engine. Approximately 500 ng of total RNA was used for each reaction. Reactions were composed as follows: 4 µl 5× q-Script Reaction Mix plus 3-5 µl nuclease-free water plus 1 µl q-Script Reverse Transcriptase plus 10-12 µl input RNA. After mixing, reactions were centrifuged at 3750 rpm for 2 minutes at room temperature and run on a "q-Script" protocol (25° C. for 5 minutes, followed by 42° C. for 30 minutes, and then 85° C. for 5 minutes) in a MJ Research thermocycler. Each reaction was diluted with 30 µl of nuclease-free water and used immediately for SYBR-green Q-PCR or stored at −20° C. SYBR-Green Q-PCR reactions were performed as follows. Reaction mixtures for the LXR target gene, ABCG1, and the internal standard normalization gene ribosomal protein L30 were prepared using validated forward/reverse primer sets [ABCG1 (X-Mmul-ABCG1-F1 and X-Mmul-ABCG1-R1); ribosomal protein L30 (SYBR-hL30-F1 and SYBR-hL30-R1)]. Information on sequences of these primer sets were obtained from the "Primer Bank" Web Site (http://pga.mgh.harvard.edu/primerbank/index.html) for L30 (Primer Bank #4506631a1), and from Exelixis, Inc. (South San Francisco, Calif., USA) for ABCG1 (Mmul_ABCG1.TaqMan F1/R1).

Primer Sequences

```
Mmul_ABCG1.TaqMan.F1   5'-ACGCAGACAGCACTGGTGAA-3'

Mmul_ABCG1.TaqMan.R1   5'-CTTCCCTCCACCTGGAACCT-3' hL30-F1                5'-GCTGGAGTCGATCAACTCTAGG-3' hL30-R2                5'-CCAATTTCGCTTTGCCTTGTC-3'
```

SYBR-Green reactions were assembled as follows. Per reaction, 10 µl 2× PowerSYBR® Green Supermix (Applied Biosystems Catalog #4367659) plus 2 µl of 10 µM Gene Specific Forward/Reverse Primer Mix (final concentration of primers is 500 nM each) plus 4 µl water were mixed together with 4 µl of diluted RT reaction. Reaction mixes were centrifuged at 3750 rpm for 2 minutes at room temperature and run on an Applied Biosystems model 7900HT SDS-Taqman System.

Calculation of Relative mRNA Quantities, and In Vivo Compound Potencies and Maximal Activities.

The relative amount of ABCG1 mRNA was calculated using the second derivative comparative Ct method ($2^{-\Delta\Delta C_t}$). Quantification was obtained after normalization to ribosomal protein L30 mRNA. Each sample was tested in duplicate and the average Ct was used for calculations.

Calculation of In Vivo Potency of Compounds in Cynomolgus Monkeys.

The concentration of test compound in plasma from each individual animal at 5 hrs post-dose was plotted vs. the fold induction vs. baseline of ABCG1 mRNA in blood cells for each animal at 5 hrs post-dose for all dose groups. Data from all dose groups were included on the same plot for each compound. The in vivo potency ($EC_{50}$) and maximum induction of ABCG1 mRNA for each compound was determined by non-linear curve fitting using a sigmoidal dose-response equation (Graphpad Prism 4.03 software).

Quantitation of Plasma Compound Concentrations by LC/MS/MS.

The following are details of the liquid chromatography with tandem mass spectrometry (LC/MS/MS)-based bioanalytical methods used to quantitate test compounds in cynomolgus monkey plasma.

The LC/MS/MS analysis of the test compound was conducted against a standard curve ranging from 1 to 5000 nM. The standard curves were fitted with a linear regression weighted by reciprocal squared ($1/x^2$). Standards were analyzed in single replicates. Quality control samples were prepared in blank biological matrix at 3 concentrations within the range of the standard curve and were analyzed as replicates within each analytical set. The determined concentrations of more than 75% of the QCs were within 20% of their nominal values.

Sample preparation was conducted on Janus 8-tip and Janus Mini 96-tip automated liquid handlers. Aliquots (50 µL) of the biological matrix (plasma) from in vivo studies and standard/QC samples were treated with 1 M ammonium carbonate in water pH 9.2 unadjusted (50 µL) containing 200 nM of two internal standards (IS), followed by 300 µL methyl t-butyl ether (MTBE) and partitioned by liquid-liquid extraction (LLE) using forty fill-expel tip repetitions for approximately 3 minutes. The aqueous and organic layers were then centrifuged for 2-min at 3900 rpm. The top organic layer extraction solvent MTBE (250 µL) was removed to another clean 96-well plate and placed in a nitrogen evaporator for 15 min at 40° C. to dryness. Aliquots (100 µL) were used to reconstitute the dry extracts with mobile phase consisting of 1:1 acetonitrile/water. A 10 µL aliquot was first injected onto the high-Turboflow performance liquid chromatography (HTLC) extraction column, then eluted onto a second high-performance liquid chromatography (HPLC) column for LC/MS/MS-based analysis.

The LC system used for all analyses was an Aria TX-2 (Thermo Scientific, Waltham, Mass., USA) HPLC system consisting of 8 Shimadzu LC10AD pumps with 2 SCL-10 AVP System Controllers (Columbia, Md., USA) and a dual arm CTC Analytics HTS PAL autosampler (Switzerland) equipped with a cooling stack that maintained samples at 10° C. during analysis. The HPLC on-line extraction column was a Cyclone-P mixed polymer (0.5×50 mm, 50 µM particle, Thermo Scientific, Waltham, Mass., USA) kept at room temperature. The HPLC C18 analytical column used was an XBridge C18 (2.1 mm×50 mm, 5 µM particle, Waters Corporation, Milford, Mass., USA) kept at room temperature. The mobile phase, which consisted of 0.1% formic acid in water (A) and 0.1% formic acid in acetonitrile (B), was delivered at a flow rate of 1.5 mL/min to the HTLC on-line extraction column and at 0.5 mL/min to the HPLC C18 analytical column. These flow rates change during the transfer step between 0.5 to 1.0 min. The retention times for the test compounds and internal standards were recorded. The total analysis time was 5.0 min. The gradients are summarized in the following tables.

| Mobile Phase Gradient for HPLC C18 XBridge Analytical Column | | | | |
|---|---|---|---|---|
| Time (min) | % A | % B | Flow Rate (mL/min) | Curve |
| 0 (Initial) | 95 | 5 | 0.5 | isocratic |
| 0.50 | 95 | 5 | 0.3 | isocratic |
| 1.00 | 95 | 5 | 0.3 | isocratic |
| 1.10 | 95 | 5 | 0.5 | isocratic |
| 2.00 | 5 | 95 | 0.5 | linear |
| 2.50 | 5 | 95 | 0.5 | isocratic |
| 2.60 | 95 | 5 | 0.5 | step |

| Mobile Phase Gradient for HTLC On-Line Extraction Cyclone-P Column | | | | |
|---|---|---|---|---|
| Time (min) | % A | % B | Flow Rate (mL/min) | Curve |
| 0 (Initial) | 100 | 0 | 1.5 | isocratic |
| 0.50 | 100 | 0 | 0.2 | isocratic |
| 1.00 | 100 | 0 | 0.2 | isocratic |

| Mobile Phase Gradient for HPLC C18 XBridge Analytical Column | | | | |
|---|---|---|---|---|
| Time (min) | % A | % B | Flow Rate (mL/min) | Curve |
| 1.10 | 0 | 100 | 1.5 | step |
| 2.00 | 0 | 100 | 1.5 | isocratic |
| 2.10 | 50 | 50 | 1.5 | step |
| 2.50 | 50 | 50 | 1.5 | isocratic |
| 2.60 | 100 | 0 | 1.5 | step |

The mass spectrometer used for all analyses was a Finnigan Quantum Ultra tandem mass spectrometer (Thermo Scientific, Waltham, Mass., USA) equipped with a heated electrospray interface operating in both positive and negative ionization modes. Ultra-high-purity (UHP) nitrogen was used as the sheath and aux gases at flow rates of 55 psi for sheath and 25 units for aux. The desolvation temperature was 350° C. and the source temperature was 350° C. Detection of each analyte was achieved through selected reaction monitoring (SRM). Positive ionization mode was used to quantitate the test compound and the internal standard. UHP argon at a pressure of $1.5 \times 10^{-3}$ torr was maintained in the collision cell of quadrupole 2. The transitions monitored for a compound of the present invention and its internal standard were recorded.

The in vivo potency in cynomologus monkey of test compounds, and the maximum ABCG1 induction derived from plots of plasma compound concentration at 5 hrs post-dose vs. fold mRNA induction at 5 hrs post-dose are shown in Table 2 below.

TABLE 2

| Compound | $EC_{50}$ ± S.E. (nM) | Maximum ABCG1 Induction (fold vs. baseline ± S.E.) |
|---|---|---|
| Compound No. 19, Table 1, WO 2007/002563 | 630 ± 168 | 12.4 ± 1.8 |
| Example 4 Present Invention | 141 ± 53 | 5.9 ± 0.8 |
| Example 9 Present Invention | 11 ± 6 | 8.9 ± 0.9 |

Examples 4 and 9 of the present invention are about four and sixty fold more potent than a compound know in the art after dosing in cynomologus monkeys. Similarly, Examples 4 and 9 induce ABCG1 mRNA in blood to a maximum of about six and nine fold compared to about twelve fold for a compound known in the art thereby demonstrating partial LXR activity in cynomologus monkey blood.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound, isotope, or pharmaceutically acceptable salt thereof, selected from the group consisting of:

| No. | Name |
|---|---|
| 1 | 2-(1-(3'-fluoro-4'-(hydroxymethyl)-5'-(methylsulfonyl)biphenyl-4-yl)-2-(2-(2-fluorophenyl)propan-2-yl)-1H-imidazol-4-yl)propan-2-ol; |
| 2 | 2-(2-(2-(2-chloro-6-fluorophenyl)propan-2-yl)-1-(3'-fluoro-4'-(hydroxymethyl)-3-methyl-5'-(methylsulfonyl)biphenyl-4-yl)-1H-imidazol-4-yl)propan-2-ol; |
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol; |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 6 | 2-(2-(2-(2-Chloro-phenyl)propan-2-yl)-1-(3,3'-difluoro-4'-hydroxymethyl-5'-(methylsulfonyl)biphenyl-4-yl)-1H-imidazol-4-yl)-propan-2-ol; |
| 7 | 2-(2-(2-(2-chloro-6-fluorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 8 | 2-{1-(3,3'-Difluoro-4'-hydroxymethyl-5'-methanesulfonyl-biphenyl-4-yl)-2-[2-(2-fluorophenyl)propan-2-yl]-1H-imidazol-4-yl}-propan-2-ol; |
| 9 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 10 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}$CD$_3$)$_2$]propan-2-ol; |
| 11 | 2-(2-(2,4-dichlorobenzyl)-1-(3,3'-difluoro-4'-(hydroxymethyl)-5'-(methylsulfonyl)biphenyl-4-yl)-1H-imidazol-4-yl)propan-2-ol; |
| 12 | 2-(1-(3,3'-difluoro-4'-(hydroxymethyl)-5'-(methylsulfonyl)biphenyl-4-yl)-2-(2-(trifluoromethyl)benzyl)-1H-imidazol-4-yl)propan-2-ol; |
| 13 | 2-(1-(3-chloro-3'-fluoro-4'-(hydroxymethyl)-5'-(methylsulfonyl)biphenyl-4-yl)-2-(2-chloro-4-fluorobenzyl)-1H-imidazol-4-yl)propan-2-ol; |
| 14 | 2-(2-(2-chloro-4-fluorobenzyl)-1-(3,3'-difluoro-4'-(hydroxymethyl)-5'-(methylsulfonyl)biphenyl-4-yl)-1H-imidazol-4-yl)propan-2-ol; |
| 15 | 2-(2-(2,4-dichlorobenzyl)-1-(3'-fluoro-4'-(hydroxymethyl)-5'-(methylsulfonyl)biphenyl-4-yl)-1H-imidazol-4-yl)propan-2-ol; |
| 16 | 2-(1-(3,3'-difluoro-4'-(hydroxymethyl)-5'-(methylsulfonyl)biphenyl-4-yl)-2-(2-fluorobenzyl)-1H-imidazol-4-yl)propan-2-ol; |
| 17 | 2-(1-(3'-fluoro-4'-(hydroxymethyl)-5'-(methylsulfonyl)biphenyl-4-yl)-2-(2-methylbenzyl)-1H-imidazol-4-yl)propan-2-ol; |
| 18 | 2-(2-(2,6-dichlorobenzyl)-1-(3'-fluoro-4'-(hydroxymethyl)-5'-(methylsulfonyl)biphenyl-4-yl)-1H-imidazol-4-yl)propan-2-ol; |
| 19 | 2-[2-(2-Chloro-5-fluoro-benzyl)-1-(3'-fluoro-4'-hydroxymethyl-5'-methanesulfonyl-biphenyl-4-yl)-1H-imidazol-4-yl]-propan-2-ol; |
| 20 | 2-[2-(2-Chloro-benzyl)-1-(3,3'-difluoro-4'-hydroxymethyl-5'-methanesulfonyl-biphenyl-4-yl)-1H-imidazol-4-yl]-propan-2-ol; [[or]] and |
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol. |

2. The compound, isotope, or pharmaceutically acceptable salt thereof, of claim 1 selected from the group consisting of:

| No. | Name |
|---|---|
| 1 | 2-(1-(3'-fluoro-4'-(hydroxymethyl)-5'-(methylsulfonyl)biphenyl-4-yl)-2-(2-(2-fluorophenyl)propan-2-yl)-1H-imidazol-4-yl)propan-2-ol; |
| 2 | 2-(2-(2-(2-chloro-6-fluorophenyl)propan-2-yl)-1-(3'-fluoro-4'-(hydroxymethyl)-3-methyl-5'-(methylsulfonyl)biphenyl-4-yl)-1H-imidazol-4-yl)propan-2-ol; |
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol; |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 6 | 2-(2-(2-(2-Chloro-phenyl)propan-2-yl)-1-(3,3'-difluoro-4'-hydroxymethyl-5'-(methylsulfonyl)biphenyl-4-yl)-1H-imidazol-4-yl)-propan-2-ol; |
| 7 | 2-(2-(2-(2-chloro-6-fluorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 8 | 2-{1-(3,3'-Difluoro-4'-hydroxymethyl-5'-methanesulfonyl-biphenyl-4-yl)-2-[2-(2-fluorophenyl)propan-2-yl]-1H-imidazol-4-y1}-propan-2-ol; |
| 9 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 10 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}$CD$_3$)$_2$]propan-2-ol; [[or]] and |
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol. |

3. The compound, isotope, or pharmaceutically acceptable salt thereof, of claim 1 selected from the group consisting of:

| No. | Name |
|---|---|
| 11 | 2-(2-(2,4-dichlorobenzyl)-1-(3,3'-difluoro-4'-(hydroxymethyl)-5'-(methylsulfonyl)biphenyl-4-yl)-1H-imidazol-4-yl)propan-2-ol; |
| 12 | 2-(1-(3,3'-difluoro-4'-(hydroxymethyl)-5'-(methylsulfonyl)biphenyl-4-yl)-2-(2-(trifluoromethyl)benzyl)-1H-imidazol-4-yl)propan-2-ol; |
| 13 | 2-(1-(3-chloro-3'-fluoro-4'-(hydroxymethyl)-5'-(methylsulfonyl)biphenyl-4-yl)-2-(2-chloro-4-fluorobenzyl)-1H-imidazol-4-yl)propan-2-ol; |
| 14 | 2-(2-(2-chloro-4-fluorobenzyl)-1-(3,3'-difluoro-4'-(hydroxymethyl)-5'-(methylsulfonyl)biphenyl-4-yl)-1H-imidazol-4-yl)propan-2-ol; |
| 15 | 2-(2-(2,4-dichlorobenzyl)-1-(3'-fluoro-4'-(hydroxymethyl)-5'-(methylsulfonyl)biphenyl-4-yl)-1H-imidazol-4-yl)propan-2-ol; |
| 16 | 2-(1-(3,3'-difluoro-4'-(hydroxymethyl)-5'-(methylsulfonyl)biphenyl-4-yl)-2-(2-fluorobenzyl)-1H-imidazol-4-yl)propan-2-ol; |
| 17 | 2-(1-(3'-fluoro-4'-(hydroxymethyl)-5'-(methylsulfonyl)biphenyl-4-yl)-2-(2-methylbenzyl)-1H-imidazol-4-yl)propan-2-ol; |
| 18 | 2-(2-(2,6-dichlorobenzyl)-1-(3'-fluoro-4'-(hydroxymethyl)-5'-(methylsulfonyl)biphenyl-4-yl)-1H-imidazol-4-yl)propan-2-ol; |
| 19 | 2-[2-(2-Chloro-5-fluoro-benzyl)-1-(3'-fluoro-4'-hydroxymethyl-5'-methanesulfonyl-biphenyl-4-yl)-1H-imidazol-4-yl]-propan-2-ol; [[or]] and |
| 20 | 2-[2-(2-Chloro-benzyl)-1-(3,3'-difluoro-4'-hydroxymethyl-5'-methanesulfonyl-biphenyl-4-yl)-1H-imidazol-4-yl]-propan-2-ol. |

4. The compound, isotope, or pharmaceutically acceptable salt thereof, of claim 1 selected from the group consisting of:

| No. | Name |
|---|---|
| 3 | 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol; |
| 4 | 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 5 | 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol; |
| 9 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol; |
| 10 | 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)[($^{13}CD_3$)$_2$]propan-2-ol; [[or]] and |
| 21 | 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol. |

5. A compound, isotope, or pharmaceutically acceptable salt thereof, which is 2-(1-(3-chloro-3'-fluoro-4'-(hydroxymethyl)-5'-(methylsulfonyl)biphenyl-4-yl)-2-(2-(2,6-dichlorophenyl)propan-2-yl)-1H-imidazol-4-yl)propan-2-ol.

6. The compound, isotope, or pharmaceutically acceptable salt thereof of claim 4, which is 2-(2-(2-(2-chloro-3-fluorophenyl)propan-2-yl)-1-(3'-fluoro-4'-(hydroxymethyl)-5'-(methylsulfonyl)biphenyl-4-yl)-1H-imidazol-4-yl)propan-2-ol.

7. The compound, isotope, or pharmaceutically acceptable salt thereof of claim 4, which is 2-(2-(2-(2,6-dichlorophenyl)propan-2-yl)-1-(3'-fluoro-4'-(hydroxymethyl)-5'-(methylsulfonyl)biphenyl-4-yl)-1H-imidazol-4-yl)propan-2-ol.

8. A compound, isotope, or pharmaceutically acceptable salt thereof, which is 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol.

9. The compound, isotope, or pharmaceutically acceptable salt thereof of claim 4, which is 2-{2-[1-(2,6-dichlorophenyl)ethyl]-1-[3,3'-difluoro-4'-(hydroxymethyl)-5'-(methylsulfonyl)biphenyl-4-yl]-1H-imidazol-4-yl}propan-2-ol.

10. A pharmaceutical composition comprising a compound, isotope, or pharmaceutically acceptable salt thereof of any one of claims 1 to 9 and one or more pharmaceutically acceptable carriers.

11. A method of treating a disease or disorder comprising administering to a subject in need thereof a therapeutically effective amount of a compound, isotope, or pharmaceutically acceptable salt thereof of claim 1, wherein the disease or disorder is atherosclerosis, insulin resistance, osteoarthritis, stroke, hyperglycemia, dyslipidemia, psoriasis, age and UV exposure-related skin wrinkling, diabetes, cancer, Alzheimer's disease, inflammation, immunological disorders, lipid disorders, obesity, macular degeneration, conditions characterized by a perturbed epidermal barrier function, conditions of disturbed differentiation or excess proliferation of the epidermis or mucous membrane, or cardiovascular disorders.

12. The method of claim 11 wherein the disease or disorder is atherosclerosis, diabetes, Alzheimer's disease or dyslipidemia.

13. The method of claim 11 wherein the disease or disorder is atherosclerosis.

14. The method of claim 11 wherein the disease or disorder is diabetes.

15. The method of claim 11 wherein the disease or disorder is Alzheimer's disease.

16. A pharmaceutical composition comprising a compound, isotope, or pharmaceutically acceptable salt thereof of claim 4 and one or more pharmaceutically acceptable carriers.

17. A method of treating a disease or disorder comprising administering to a subject in need thereof a therapeutically effective amount of a compound, isotope, or pharmaceutically acceptable salt thereof of claim 4, wherein the disease or disorder is atherosclerosis, insulin resistance, osteoarthritis, stroke, hyperglycemia, dyslipidemia, psoriasis, age and UV exposure-related skin wrinkling, diabetes, cancer, Alzheimer's disease, inflammation, immunological disorders, lipid disorders, obesity, macular degeneration, conditions characterized by a perturbed epidermal barrier function, conditions of disturbed differentiation or excess proliferation of the epidermis or mucous membrane, or cardiovascular disorders.

18. The method of claim 17 wherein the disease or disorder is atherosclerosis, diabetes, Alzheimer's disease or dyslipidemia.

19. A pharmaceutical composition comprising a compound, isotope, or pharmaceutically acceptable salt thereof of claim 5 and one or more pharmaceutically acceptable carriers.

20. A method of treating a disease or disorder comprising administering to a subject in need thereof a therapeutically effective amount of a compound, isotope, or pharmaceutically acceptable salt thereof of claim 5, wherein the disease or disorder is atherosclerosis, insulin resistance, osteoarthritis, stroke, hyperglycemia, dyslipidemia, psoriasis, age and UV exposure-related skin wrinkling, diabetes, cancer, Alzheimer's disease, inflammation, immunological disorders, lipid disorders, obesity, macular degeneration, conditions characterized by a perturbed epidermal barrier function, conditions of disturbed differentiation or excess proliferation of the epidermis or mucous membrane, or cardiovascular disorders.

21. The method of claim 20 wherein the disease or disorder is atherosclerosis, diabetes, Alzheimer's disease or dyslipidemia.

22. The method of claim 20 wherein the disease or disorder is atherosclerosis.

23. The method of claim 20 wherein the disease or disorder is diabetes.

24. The method of claim 20 wherein the disease or disorder is Alzheimer's disease.

25. A pharmaceutical composition comprising a compound, isotope, or pharmaceutically acceptable salt thereof of claim 8 and one or more pharmaceutically acceptable carriers.

26. A method of treating a disease or disorder comprising administering to a subject in need thereof a therapeutically effective amount of a compound, isotope, or pharmaceutically acceptable salt thereof of claim 8, wherein the disease or disorder is atherosclerosis, insulin resistance, osteoarthritis, stroke, hyperglycemia, dyslipidemia, psoriasis, age and UV exposure-related skin wrinkling, diabetes, cancer, Alzheimer's disease, inflammation, immunological disorders, lipid disorders, obesity, macular degeneration, conditions characterized by a perturbed epidermal barrier function, conditions of disturbed differentiation or excess proliferation of the epidermis or mucous membrane, or cardiovascular disorders.

27. The method of claim 26 wherein the disease or disorder is atherosclerosis, diabetes, Alzheimer's disease or dyslipidemia.

28. The method of claim 26 wherein the disease or disorder is atherosclerosis.

29. The method of claim 26 wherein the disease or disorder is diabetes.

30. The method of claim 26 wherein the disease or disorder is Alzheimer's disease.

* * * * *

UNITED STATES PATENT AND TRADEMARK OFFICE
CERTIFICATE OF CORRECTION

PATENT NO.       : 8,618,154 B2                                         Page 1 of 1
APPLICATION NO.  : 13/319937
DATED            : December 31, 2013
INVENTOR(S)      : Brett B. Busch et al.

It is certified that error appears in the above-identified patent and that said Letters Patent is hereby corrected as shown below:

In the Claims:

Claim 1:

Column 73, line 63, change "[[or]] and" to -- and --.

Claim 2:

Column 74, line 35, change "[[or]] and" to -- and --.

Claim 3:

Column 74, line 64, change "[[or]] and" to -- and --.

Claim 4:

Column 75, line 18, change "[[or]] and" to -- and --.

Signed and Sealed this
Thirteenth Day of January, 2015

Michelle K. Lee
*Deputy Director of the United States Patent and Trademark Office*